(12) United States Patent
Tatara et al.

(10) Patent No.: US 10,835,614 B2
(45) Date of Patent: Nov. 17, 2020

(54) POLY(DIOL FUMARATES) AND POLY(DIOL FUMARATE-CO-SUCCINATES)

(71) Applicants: William Marsh Rice University, Houston, TX (US); Board of Regents, The University of Texas System, Austin, TX (US)

(72) Inventors: Alexander Mitchell Tatara, West Dundee, IL (US); Emma Watson, Wichita, KS (US); Antonios G. Mikos, Houston, TX (US); Dimitrios P. Kontoyiannis, Bellaire, TX (US)

(73) Assignees: William Marsh Rice University, Houston, TX (US); Board of Regents, The University of Texas System, Austin, TX (US)

(*) Notice: Subject to any disclaimer, the term of this patent is extended or adjusted under 35 U.S.C. 154(b) by 29 days.

(21) Appl. No.: 16/146,258

(22) Filed: Sep. 28, 2018

(65) Prior Publication Data

US 2019/0091343 A1    Mar. 28, 2019

Related U.S. Application Data

(63) Continuation of application No. PCT/US2017/025084, filed on Mar. 30, 2017.

(60) Provisional application No. 62/315,607, filed on Mar. 30, 2016.

(51) Int. Cl.
| | | |
|---|---|---|
| *A61K 47/59* | (2017.01) | |
| *A61L 27/18* | (2006.01) | |
| *A61L 27/58* | (2006.01) | |
| *C08G 63/52* | (2006.01) | |
| *A61L 27/38* | (2006.01) | |
| *A61K 47/69* | (2017.01) | |
| *A61P 31/10* | (2006.01) | |
| *A61K 31/506* | (2006.01) | |
| *A61K 47/14* | (2017.01) | |

(52) U.S. Cl.
CPC .......... *A61K 47/593* (2017.08); *A61K 31/506* (2013.01); *A61K 47/14* (2013.01); *A61K 47/6927* (2017.08); *A61L 27/18* (2013.01); *A61L 27/38* (2013.01); *A61L 27/58* (2013.01); *A61P 31/10* (2018.01); *C08G 63/52* (2013.01)

(58) Field of Classification Search
CPC .................................................. A61K 47/593
See application file for complete search history.

(56) References Cited

FOREIGN PATENT DOCUMENTS

| | | |
|---|---|---|
| JP | 2015/152818 A | 8/2015 |
| WO | WO 2009/094375 A1 * 7/2009 | ............. C08G 63/12 |

OTHER PUBLICATIONS

Joos et al., Makromolekulare Chemie (1987), 188(6), pp. 1375-1381.*
Jacovic et al., Makromolekulare Chemie (1988), 189(6), pp. 1353-1362.*
Nikolic, MS et al. "Synthesis and characterization of biodegradable poly(butylene succinate-co-butylene fumarate)s" European Polymer Journal, May 28, 2003, pp. 2183-2185.

* cited by examiner

*Primary Examiner* — Brian J Davis
(74) *Attorney, Agent, or Firm* — Matthew S. Gibson; Ryan P. Cox; Reed Smith LLP

(57) ABSTRACT

The disclosure relates to a class of diol-based, unsaturated aliphatic polyesters that biodegrade into monomers capable of mitigating infection. These poly(diol fumarates) (PDFs) and poly(diol fumarate-co-succinates) (PDFSs), can be crosslinked to form networks of scaffolds with antimicrobial degradation products. Both the diol carbon length and the degree of available double bonds are tunable, resulting in a highly controllable class of antimicrobial polymers useful for cell scaffolds and drug delivery systems and devices.

20 Claims, 32 Drawing Sheets

Monomer: Diol    Di-Acid

Structure:

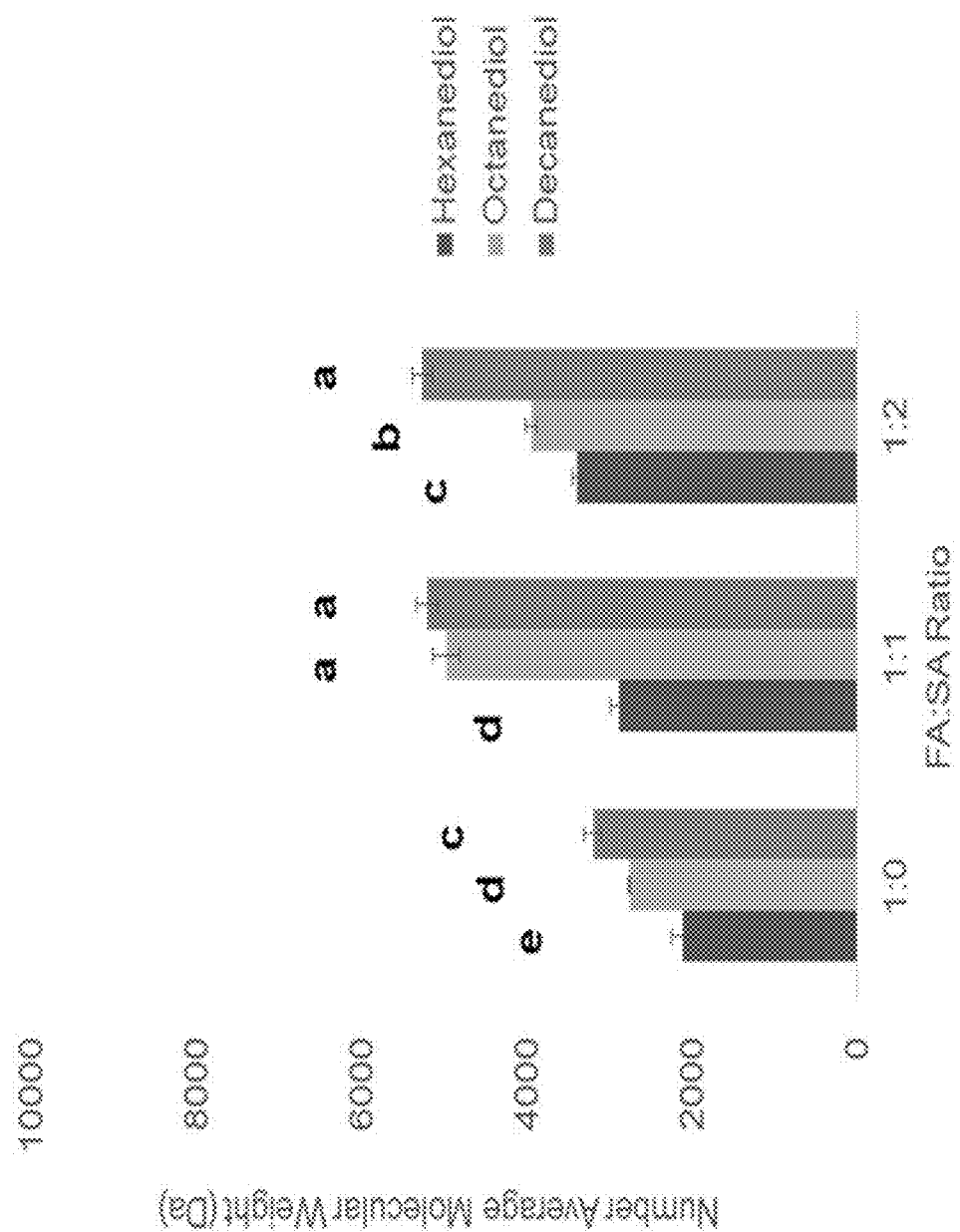

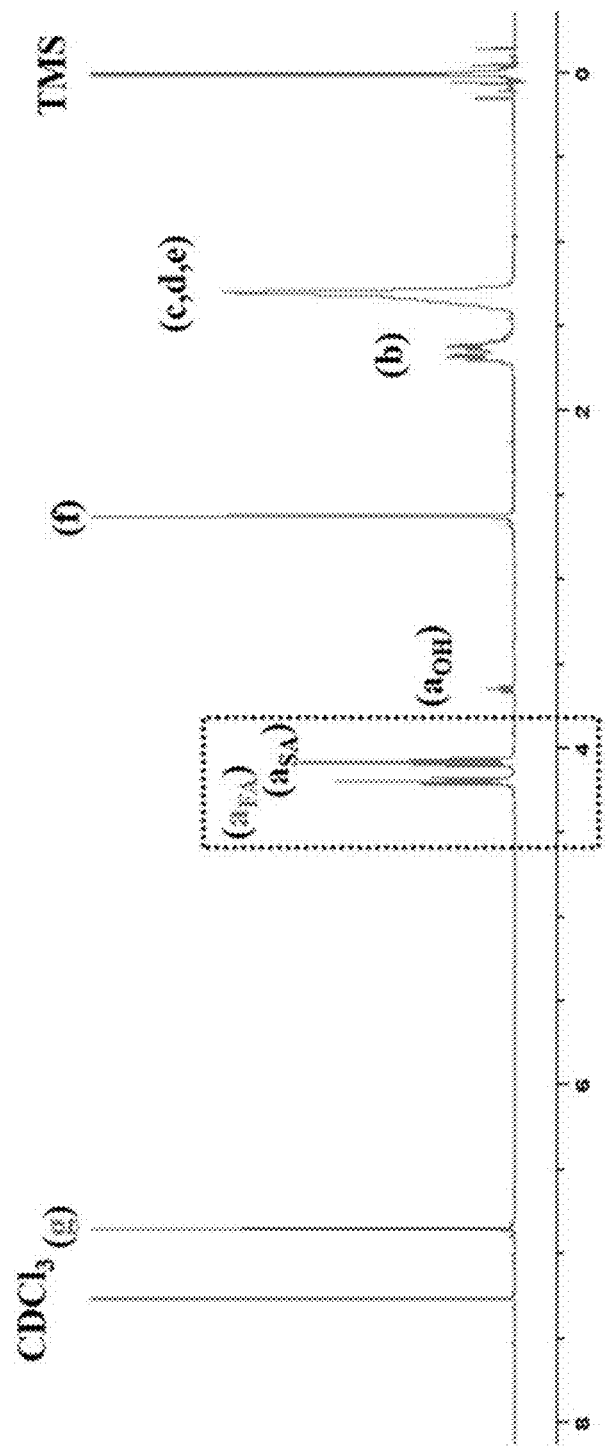

POLY(DIOL FUMARATES) AND POLY(DIOL FUMARATE-CO-SUCCINATES)

This application in a continuation of International Patent Application No. PCT/US17/25084 filed Mar. 30, 2017, which claims priority to U.S. Provisional Patent Application, Ser. No. 62/315,607, filed Mar. 30, 2016, the contents of which is incorporated herein by reference thereto.

BACKGROUND

Fungal infection is a devastating disease with high morbidity and mortality in immunocompromised populations, such as patients suffering from cancer or recovering from organ transplantation. New therapies are direly needed to address the high lethality and increasing level of antimicrobial resistance associated with species such as *Aspergillus fumigatus*.

Given the propensity of *Aspergillus* to invade and destroy local vasculature, tissue defects with fungal infection may be difficult to treat by systemic antifungal therapy due to lack of sufficient circulation carrying therapeutics to the site of infection. Systemic therapy is not superior to surgical therapy in preventing mortality in cutaneous aspergillosis, for example. Therefore, targeted and/or local therapy is an attractive option for the treatment of tissue defects with fungal infection. Microparticle-based drug delivery systems have been explored for local delivery of antibiotics and have been successfully translated and commercialized for use in the clinic.

Biodegradable synthetic macromers serve as useful platforms for the design of drug delivery vehicles and tissue scaffolds in biomedical settings. Aliphatic polyesters are seeing increasing use in medical devices due to their ability to be degraded hydrolytically under physiologic conditions. Specific aliphatic polyesters such as poly(propylene fumarate) and oligo(poly(ethylene glycol) fumarate) contain carbon-carbon double bonds within the polymer backbone. These unsaturated bonds act as potential sites for modification and/or crosslinking to build three dimensional polymer networks.

Due to the tremendous healthcare burden of device-related infections, novel biomaterials and strategies for prevention of pathogenic device colonization are warranted.

SUMMARY

The present disclosure relates to a class of unsaturated biodegradable aliphatic esters composed of alternating terminal diol and fumarate and/or succinate, namely poly(diol fumarates) (PDFs) and poly(diol fumarate-co-succinates) (PDFSs). These polymers present a wide range of physicochemical properties based on synthesis conditions, the length of the terminal diol chosen, and the ratio of fumarate to succinate within the polymer backbone. As the polymer biodegrades by hydrolysis, it produces free diols, fumaric acid, and/or succinic acid.

In one aspect, the invention provides a polymer comprising condensed units of an aliphatic terminal diol and two dicarboxylic acids; wherein the terminal diol comprises from 6 to 10 methylene groups and the dicarboxylic acids comprise fumaric acid and succinic acid wherein the ratio of fumaric acid to succinic acid is from 1:0.8 to 1:4.

Embodiments of the polymer include those wherein the aliphatic terminal diol is selected from the group consisting of 1,6-hexanediol, 1,8-octanediol, or 1,10-decanediol; and/or wherein the polymer consists essentially of the diol and the two dicarboxylic acids.

In another aspect, the invention provides a composition comprising a polymer comprising condensed units of an aliphatic terminal diol and an unsaturated dicarboxylic acid; wherein the terminal diol comprises a divalent alkane chain having a length of 6 to 10 carbon atoms with a terminal hydroxyl group on each end; and the dicarboxylic acid comprises fumaric acid; wherein the polymer is crosslinked; such as where a three dimensional network is formed.

Embodiments of the crosslinked polymer composition include those wherein the polymer further comprises condensed units of succinic acid; wherein the ratio of fumaric acid units to succinic acid units is from 1:0.8 to 1:4; wherein the aliphatic terminal diol is selected from the group consisting of 1,6-hexanediol, 1,8-octanediol, or 1,10-decanediol; wherein the aliphatic terminal diol is 1,10-decanediol; wherein the polymer is selected from the group consisting of poly(hexanediol fumarate), poly(hexanediol fumarate-co-succinate), poly(hexanediol fumarate-co-succinate), poly(octanediol fumarate), poly(octanediol fumarate-cosuccinate), poly(octanediol fumarate-co-succinate), poly(decanediol fumarate), poly(decanediol fumarate-co-succinate), and poly(decanediol fumarate-co-succinate); and/or wherein the polymer consists essentially of condensed units of the diol, fumaric acid and succinic acid.

In another aspect, the invention provides a drug delivery device comprising a polymer and a therapeutic agent, wherein the polymer comprises condensed units of an aliphatic terminal diol and an unsaturated dicarboxylic acid; wherein the terminal diol comprises a divalent alkane chain having a length of 6 to 10 carbon atoms with a terminal hydroxyl group on each end; and the dicarboxylic acid comprises fumaric acid.

Embodiments of the drug delivery device include those wherein the polymer further comprises condensed units of succinic acid; wherein the ratio of fumaric acid units to succinic acid units is from 1:0.8 to 1:4; wherein the aliphatic terminal diol is selected from the group consisting of 1,6-hexanediol, 1,8-octanediol, or 1,10-decanediol; wherein the aliphatic terminal diol is 1,10-decanediol; wherein the polymer is selected from the group consisting of poly(hexanediol fumarate), poly(hexanediol fumarate-co-succinate), poly(hexanediol fumarate-co-succinate), poly(octanediol fumarate), poly(octanediol fumarate-cosuccinate), poly(octanediol fumarate-co-succinate), poly(decanediol fumarate), poly(decanediol fumarate-co-succinate), and poly(decanediol fumarate-co-succinate); and/or wherein the polymer is poly(decanediol fumarate).

Embodiments of the drug delivery device comprising any of the polymer embodiments described above include those wherein the therapeutic agent comprises a triazole antifungal agent; and/or wherein the therapeutic agent comprises voriconazole.

An embodiment of the drug delivery device comprising any of the embodiments described above comprises a microparticle comprising the polymer and the therapeutic agent.

In another aspect, the invention provides a method for treatment of a subject suffering a fungal infection comprising application of the drug delivery device of any of the embodiments described above to the site of the fungal infection.

Embodiments of the method include those wherein the fungal infection comprises any of aspergillosis, candidemia, candidiasis, mucormycosis, *fusarium* infection, or scedosporium infection.

In another aspect, the invention provides a cellular scaffold comprising a polymer and a cell, wherein the polymer comprises a polymer comprising condensed units of an aliphatic terminal diol and an unsaturated dicarboxylic acid; wherein the terminal diol comprises from 6 to 10 methylene groups and the dicarboxylic acid comprises fumaric acid.

Embodiments of the cellular scaffold include those wherein the polymer further comprises condensed units of succinic acid; wherein the ratio of fumaric acid units to succinic acid units is from 1:0.8 to 1:4; wherein the aliphatic terminal diol is selected from the group consisting of 1,6-hexanediol, 1,8-octanediol, or 1,10-decanediol; wherein the aliphatic terminal diol is 1,10-decanediol; wherein the polymer is selected from the group consisting of poly(hexanediol fumarate), poly(hexanediol fumarate-co-succinate), poly(hexanediol fumarate-co-succinate), poly(octanediol fumarate), poly(octanediol fumarate-cosuccinate), poly(octanediol fumarate-co-succinate), poly(decanediol fumarate), poly(decanediol fumarate-co-succinate), and poly(decanediol fumarate-co-succinate); wherein the polymer consists of condensed units of the diol, fumaric acid and succinic acid; and/or wherein the polymer is crosslinked.

In another aspect, the invention provides a pharmaceutical composition comprising a polymer described herein, a therapeutic agent as an active ingredient and optionally, a pharmaceutically acceptable carrier and/or excipient or diluent.

Embodiments of the pharmaceutical compositions may further include a pharmaceutical surfactant such as a cationic surfactant, an anionic surfactant, and/or a non-ionic surfactant. Embodiments of the pharmaceutical compositions may further include a cryoprotectant.

In some embodiments, pharmaceutical composition including a polymer described herein, a therapeutic agent and a pharmaceutically acceptable excipient, such as a salt or a diluent.

The pharmaceutical composition may comprise microparticles of the polymers described herein, particularly microparticles that comprise the polymer and a therapeutic agent, such as a triazole antifungal agent, such as voriconazole.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

FIG. 5A is a bar graph demonstrating the relationship between diol and FA:SA ratio on number average molecular weight (n=3) of PDFs synthesized for 24 hr at 120° C. in the presence of 1 mol % PTSA. Those that do not share a letter are significantly different ($p<0.05$).

FIG. 10A shows the $^1$H NMR (CDCl$_3$, with 1% v/v TMS, 400 MHz) spectrum of P10F50 (δ 1.29 (m, 12H), 1.64 (dt, 4H, J=24.1 Hz), 2.62 (s, 4H), 3.64 (t, 1H, J=7.2 Hz), 4.08 (t, 4H, J=7.2 Hz), 4.19 (t, 4H, J=7.2 Hz), 6.85 (s, 2H)).

DETAILED DESCRIPTION

As used herein, the term "biodegradable" refers to the ability of a composition to be broken down, particularly into innocuous products by the action of living organisms.

Polymer Structure

Figure 1:
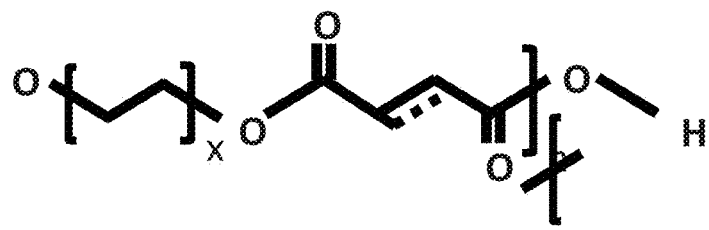
FIG. 1 depicts the structure of the poly(diol fumarates) (PDFs) and poly(diol fuamarate-co-succinates) (PDFSs).
Figure 2A:
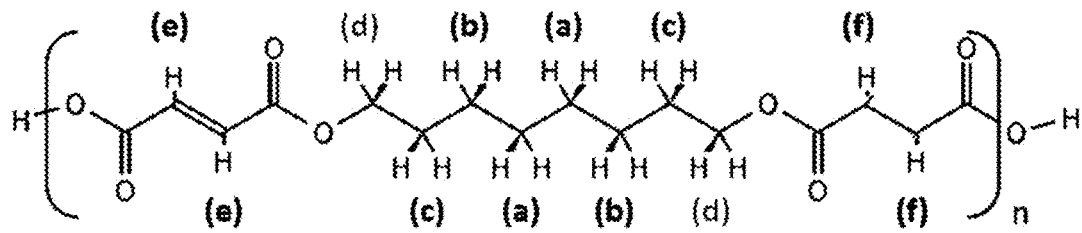
FIG. 2A depicts the structure of poly(octanediol fumarate-co-succinate) of n units.

This invention relates to polyesters and copolyesters obtained from aliphatic dicarboxylic acids and aliphatic diols. The poly(diol fumarates) (PDFs) and poly(diol fumarate-co-succinates) (PDFSs) comprise a terminal diol (such as but not limited to 1,6-hexanediol, 1,8-octanediol, or 1,10-decanediol) and a dicarboxylic acid (either fumaric acid, succinic acid, or a combination of the two) as shown in FIG. 1, wherein x is an integer from 6-10, and the bond between the carbonyl groups can be a single bond (for a succinic moiety) or a double bond (for a fumaric moiety). By choosing diols of different lengths, the final properties of the polymer can be altered. In addition, by altering the ratio of fumaric acid to succinic acid, the number of unsaturated carbon-carbon double bonds available for additional chemistries can be modified. FIG. 2A depicts an idealized structure of poly(octanediol fumarate-co-succinate) of n units, wherein the amounts of the fumarate and succinate moieties are equal and evenly distributed throughout the polymer chain. As discussed in more detail below, the amounts and distribution of the dicarboxylic acid moieties in the polymer chain can vary.

Given that the ester bonds between each diol and dicarboxylic acid are hydrolytically cleavable, these polymers are degradable in aqueous solutions (such as when implanted in the body). By choosing different diols (or combinations of diols) as well as different ratios of the two dicarboxylic acids, a family of biodegradable polymers with a diverse set of physicochemical properties is available.

The polymers described herein may comprise small amounts (less than 5, or less than 1 mol %) of other monomers that may be useful in modifying the properties of the polymer. Notably the polymers consist essentially of condensed units of the diol, fumaric acid and optionally succinic acid, and no other units derived from other monomers. Notable polymers contain no moieties derived from citrate or carbonate monomers.

Polymer Synthesis

Polyesters in general are prepared by polycondensation of alcohols with carboxylic acids or their polyester-forming derivatives. The PDFs and PDFSs can be synthesized in the same manner by Fischer esterification. They can be prepared by modification of known processes, for example by catalytically condensing the dicarboxylic acids or their polyester-forming derivatives together with the diols. Esterification catalysts may be used to accelerate the reaction. Suitable esterification catalysts are organic and inorganic acids, for example p-toluene sulfonic acid, hydrochloric acid or concentrated sulfuric acid. P-Toluene sulfonic acid is preferred. Other suitable esterification catalysts are bases and even metal salts, for example antimony, tin, titanium and lead compounds. Other polycondensation catalysts include titanium isopropoxide, manganese diacetate, antimony oxide, dibutyl tin diacetate, zinc chloride, or combinations thereof. The amount of catalyst to obtain an acceptable synthesis rate at the desired temperatures will vary, and can be determined by experimentation. The catalysts are typically employed in amounts from 10 to 5000, or 10 to 1000 parts per million (ppm), based on total weight of the reactants. In general, the process conditions are chosen so that polyesters are obtained that have a statistically random distribution of the monomers. However, it is also possible to follow a procedure such that block polyesters are obtained, by, for example, subjecting precondensates of homopolyesters (for example polyhexamethylene fumarate, polyhexamethylene succinate) in appropriate quantity ratios to a polycondensation reaction.

As used herein, the term "condensed units" refers to the moieties incorporated into the polymer backbone or chain (in which the diol(s) and dicarboxylic acid(s) form ester linkages) that are derived from the named comonomer. For example, a condensed unit of a diol is the moiety comprising the oxygen atoms of the precursor diol and the intervening methylene moieties.

Acid-forming derivatives are understood as meaning, for example, the dicarboxylic acid dihalides, preferably the chlorides, and the dicarboxylic acid esters, for example the lower alkyl esters and phenyl esters.

Known embodiments of the process are, for example, solution of azeotropic condensation, interfacial condensation melt condensation or solid phase condensation and also combinations of these methods. The process is generally carried out at temperatures of 50 to 300 C, under normal pressure, in vacuo and/or in a stream of inert gas, depending on which monomers are employed.

Briefly, equimolar concentration of terminal diol and dicarboxylic acid can be heated together at high temperature, such as greater than 120° C. under a nitrogen atmosphere for condensation and polymerization to occur. The temperature and duration of heating affect the final properties of the polymer. P-toluenesulfonic acid (PTSA) can be added in small quantities (0.1-1 mol %) as a catalyst to increase polymerization without increasing temperature or duration of heating. Upon cooling to room temperature, the resulting raw polymer is a waxy resin of white to gray color, depending on the diol and dicarboxylic acids chosen. As is common to Fischer esterifications, this raw polymer may contain some unreacted monomer components (diol and dicarboxylic acid or derivative). The raw polymer can be purified by well-known techniques such as partitioning the polymer and unreacted monomers between organic and aqueous solvents. To prevent degradation, the purified polymer may be stored under dry conditions and shielded from light.

The polyester synthesis and compositions prepared thereby may be modified by including small amounts of additives know in the polyester art as quenchers, chain extenders, branching agents, polymerization inhibitors and/ or antioxidants. Generally, a quencher is selected from phosphoric acid, phosphorous acid, boric acid, and combinations thereof. In an embodiment of the method, the quencher is added at from 0.05 to 1 mole % based upon total moles of polymer. Chain extenders may selected from mononuclear isocyanate, binuclear isocyanate, trinuclear isocyanate, tetra or higher nuclear isocyanate and their mixtures, diisocyanate selected from the group consisting of tolylene 2,4-diisocyanate, tolylene 2,6-diisocyanate, 2,4'-diphenylmethane diisocyanate, naphthylene-1,5-diisocyanate, xylylene diisocyanate, hexamethylene diisocyanate, isophorone diisocyanate, and methylenebis (2-isocyanatocyclohexane). Branching agents include polyfunctional organic compounds containing greater than or equal to three functional groups selected from hydroxyl, carboxyl, carboxylic anhydride, haloformyl, and mixtures of the foregoing functional groups. Specific examples include trimellitic acid, trimellitic anhydride, trimellitic trichloride (TMTC), tris-p-hydroxy phenyl ethane (THPE), 3,3-bis-(4-hydroxyphenyl)-oxindole (also known as isatin-bis-phenol), tris-phenol TC (1,3,5-tris((p-hydroxyphenyl)isopropyl)benzene), tris-phenol PA (4(4(1,1-bis(p-hydroxyphenyl)-ethyl) alpha,alpha-dimethyl benzyl)phenol), 4-chloroformyl phthalic anhydride, trimesic acid, and benzophenone tetracarboxylic acid. The branching agents can be added at a level of 0.05 to 2.0 wt. %.

To protect the polyesters against unwanted premature crosslinking, polymerization inhibitors or antioxidants may be added to them during their preparation. Suitable stabilizers are compounds normally used to prevent thermal polymerization, for example phenols and phenol derivatives, preferably sterically hindered phenols, amines, nitrosamines, quinones, hydroquinone monoalkyl ethers, phenothiazines or phosphoric acid esters. They may be generally used in quantities of 0.001 to 3% by weight and preferably in quantities of 0.005 to 0.5% by weight. Toluhydroquinone in a concentration of 0.01 to 0.05% by weight may be suitable.

More specifically, the polymers of the present disclosure possess the ability to be modified by changing the number of carbons in the diol chosen, and ability to be modified by altering the double bond density through increasing or decreasing the ratio of fumaric acid to succinic acid. As a result of the unsaturated double bond in the fumarate group of the PDFs and PDFSs, chemistries such as free radical reactions or click reactions allow for functionalization of the polymer. For example, this can be used to create crosslinked networks, or to attach different cell-recognition/adhesion motifs to the surface of the polymer.

Given the wide variety of physicochemical properties, ability to attach functional groups, and biodegradable nature of the PDFs and PDFSs, the compositions of the present disclosure are useful as, for example, a cellular scaffold or drug delivery device for biomedical applications.

The polymers described herein can be used to provide drug delivery systems or devices, or pharmaceutical compositions, wherein the polymers are combined with a therapeutic agent.

The drug delivery systems or devices or pharmaceutical compositions of the present invention encompass compositions made by admixing a polymer or composition of the present invention and a therapeutic agent and optionally a pharmaceutically acceptable carrier and/or excipient or diluent. Such compositions are suitable for pharmaceutical use in an animal or human.

The pharmaceutical compositions of the invention include a polymer or composition described herein, a therapeutic agent as an active ingredient and optionally, a pharmaceutically acceptable carrier and/or excipient or diluent.

The compounds of the present invention can be combined with a therapeutic agent in intimate admixture optionally with a suitable pharmaceutical carrier and/or excipient according to conventional pharmaceutical compounding techniques. Any carrier and/or excipient suitable for the form of preparation desired for administration is contemplated for use with the polymers disclosed herein. The compositions may be prepared by any of the methods well well-known in the art of pharmacy.

The compositions include compositions suitable for topical, parenteral, pulmonary, nasal, rectal or oral administration. The most suitable route of administration in any given case will depend in part on the nature and severity of the conditions being diagnosed. Other preferred compositions include compositions suitable for systemic (enteral or parenteral) administration. Systemic administration includes oral, rectal, sublingual, or sublabial administration. The compositions may be administered by injection, e.g., via a syringe, subcutaneously, intravenously, intramuscularly, or intraperitoneally.

Compositions for pulmonary administration include, but are not limited to, dry powder compositions comprising the powder of a polymer described herein with a therapeutic agent, and optionally the powder of a suitable carrier and/or lubricant. The compositions for pulmonary administration can be inhaled from any suitable dry powder inhaler device known to a person skilled in the art.

Compositions for systemic administration include, but are not limited to, dry powder compositions consisting of the composition as set forth herein and optionally the powder of a suitable carrier and/or excipient. The compositions and/or drug delivery devices for systemic administration can be represented by, but not limited to, tablets, capsules, caplets, pills, syrups, solutions, and suspensions.

In some embodiments, the present invention provides compositions further including a pharmaceutical surfactant.

In some embodiments, the present invention provides compositions further including a cationic surfactant selected from the group consisting of benzalkonium chloride, benzethonium chloride, and cetrimide.

In some embodiments, the present invention provides compositions further including an anionic surfactant selected from the group consisting of docusate sodium and sodium lauryl sulfate.

In some embodiments, the present invention provides compositions further including a non-ionic surfactant selected from the group consisting of glyceryl monooleate, sorbitan esters, polyoxyethylene sorbitan fatty acid esters, and polyoxyethylene alkyl ethers. In some embodiments, the non-ionic surfactant is a sorbitan ester selected from the group consisting of sorbitan monolaurate, sorbitan monooleate, sorbitan monopalmitate, sorbitan sesquioleate, andsorbitan trioleate. In some embodiments, the non-ionic surfactant is a polyoxyethylene sorbitan fatty acid ester selected from the group consisting of polysorbate 20, polysorbate 40, polysorbate 60, polysorbate 65, polysorbate 80, and polysorbate 85. In some other embodiments, the non-ionic surfactant is a polyoxyethylene alkyl ether selected from the group consisting of polyethylene glycol monocetyl ether, polyethylene glycol monolauryl ether, polyethylene glycolmonooleyl ether, and polyethylene glycol monostearyl ether. In some embodiments, the poloxamer is selected from the group consisting of P124, P188, P237, P338, and P407. In some embodiments, the present invention provides compositions further including a cryoprotectant. In some embodiments, the cryoprotectant is selected from the group consisting of glucose, sucrose, trehalose, lactose, sodium glutamate, PVP, HPβCD, CD, glycerol, maltose, mannitol, and saccharose.

In some embodiments, the present invention provides a pharmaceutical composition including a polymer described herein, a therapeutic agent and a pharmaceutically acceptable excipient. In some of these embodiments, the pharmaceutically acceptable excipient includes a salt or a diluent.

In some embodiments, the composition is formulated for oral administration or intravenous administration and includes the composition and at least one member selected from the group consisting of an aqueous solution and a buffer solution.

The compositions, agents, and nanoparticles described herein may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), 5 suitable mixtures thereof, and vegetable oils.

Kits providing a unit dosage of the pharmaceutical compositions set forth herein are contemplated as within the present invention. Kits providing many unit dosages of the compositions set forth herein are contemplated as within the present invention. Still further, kits providing several unit dosages of the compositions set forth herein are contemplated as within the present invention. In some embodiments, the kits of the present invention include a unit dosage of a pharmaceutical compositions set forth herein. In certain embodiments, the kits of the present invention include many unit dosages of a pharmaceutical compositions set forth herein. In certain other embodiments, the kits of the present invention include a unit dosage of a pharmaceutical composition set forth herein.

Administration of an appropriate amount of the pharmaceutical composition may be by any means known in the art such as, for example, oral or rectal, parenteral, intraperitoneal, intravenous, subcutaneous, subdermal, intranasal, or intramuscular.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

Injection solutions and suspensions can be prepared from sterile powders, granules, and tablets of the kind previously described. Formulations suitable for parenteral administration, such as, for example, by intra-articular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In the pharmaceutical compositions of the present invention for oral, sublingual, subcutaneous, intramuscular, intravenous, local or rectal administration, the active principle, polymers in association with a therapeutic agent, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

Drug delivery devices of the invention comprise powders, microparticles, tablets, gelatin capsules, pills, capsules, caplets, sachets and the like as described herein comprising a polymer described herein, optionally crosslinked, and a therapeutic agent. Drug delivery devices also include shaped articles comprising the polymers, optionally crosslinked, and a therapeutic agent, including for example films, disks or rods. Such shaped articles may be suitable for implantation in a subject's body, such as subcutaneously. Drug delivery devices also include devices comprising a substrate such as a polymeric film, metallic foil, woven or knitted fabric, nonwoven textile, cellulosic material comprising paper or cellulose fibers, or combinations thereof, coated with a polymer described herein, optionally crosslinked, and a therapeutic agent. Such devices may be used as bandages, dressings, transdermal patches and the like. Drug delivery devices also include devices configured to deliver one or more unit dosages of a pharmaceutical composition comprising a polymer described herein, optionally crosslinked, and a therapeutic agent. Such devices include for example, syringes, aerosol sprayers, pump sprayers, applicators, or inhalers. In any of the devices described herein, the therapeutic agent may be dispersed in a matrix comprising a polymer described herein, such as in a microparticle. Alternatively, the therapeutic agent may be contained, but not dispersed, within a component comprising the polymer. For example, particles of the therapeutic agent may be coated with the polymer.

As described herein, the polymers may comprise condensed units of diols that provide antifungal or antimycotic activity. Accordingly, the polymers described herein may be particularly useful in treating fungal infections, especially when used in combination with an antimycotic or antifungal therapeutic agent. Notable antimycotic agents include triazole antifungal agents, such as voriconazole.

The pharmaceutical composition, drug delivery device or drug delivery system may comprise microparticles of the polymers described herein, particularly microparticles that comprise the polymer and a therapeutic agent, such as a triazole antifungal agent, such as voriconazole.

The compositions are useful in treating a subject suffering a fungal infection, such as wherein the fungal infection comprises aspergillosis, candidemia, candidiasis, mucormycosis, fusarium infection, or scedosporium infection.

Notably, the composition may be applied topically to the site or locus of the fungal infection. Topical formulations may include powders, solutions, suspensions, dispersions, lotions, creams, gels and the like comprising a polymer described herein, optionally crosslinked, and a therapeutic agent. The topical formulations may be applied to the locus of the infection by, for example, spraying or coating the formulation on the locus using a suitable spray or applicator device. The topical formulation may also be applied to the locus as part of a bandage, dressing or transdermal patch.

The invention provides a method for treatment of a subject suffering a fungal infection comprising application of the pharmaceutical composition or the drug delivery device to the site of the fungal infection, such as wherein the fungal infection comprises aspergillosis, candidemia, candidiasis, mucormycosis, fusarium infection, or scedosporium infection.

Scaffolds of crosslinked PDF networks were fabricated by mixing the polymers with crosslinker (N-vinyl-2-pyrrolidinone, 1:1 mass ratio) and a photoinitiator (Irgacure 819, 0.3 wt %). The effects of different diols and availability of double bonds on the resulting Fourier Transform Infrared spectra, swelling ratios, and compressive properties of these networks were measured as previously described. For compressive testing, a mixture of PDF, crosslinker, and photoinitiator was poured into cylindrical molds (3 mm in diameter, 6 mm in height), exposed to blue light for 160 seconds to initiate crosslinking, and then compressed at a crosshead speed of 1 mm/min.

As used herein, the term "crosslinked" refers to polymer composition in which a first portion of a polymer chain is covalently linked to another second remote portion of a polymer chain by a "crosslinker" that forms a bridge or link between the two portions. The first and second portions may be on the same polymer chain or on two polymer chains. The crosslinker may be a direct bond, or may comprise a moiety comprising one or more atoms suitable for covalently bonding two portions of a polymer described herein. The result of crosslinking is to provide a three-dimensional network comprising polymer chains linked together.

Alternatively or additionally, the polymers described herein may be linked to a different moiety by covalently binding a portion of the polymer to a different moiety by a linker comprising a direct bond or a moiety comprising one or more atoms suitable for covalently bonding a portion of a polymer described herein with the different moiety. The different moiety may comprise a molecule with one or more functional groups, or an oligomer or a polymer having a structure different from the polymers described herein.

Notably the polymers described herein and the crosslinked compositions prepared therefrom may be useful as cellular scaffolds or tissue scaffolds, wherein the cellular scaffold comprises the polymer or the cross linked composition and at least one cell.

Embodiments of the cellular scaffold comprise any embodiment of the polymers and/or cross linked compositions described herein.

EXAMPLES

Materials

Fumaric acid (FA), succinic acid (SA), 1,6-hexanediol, 1,8-octanediol, 1,10-decanediol, toluene (laboratory reagent grade), polystyrene standards, 1-vinyl-2-pyrrolidinone (NVP), and p-toluenesulfonic acid monohydrate (PTSA) were purchased from Sigma-Aldrich (St. Louis, Mo.). Anhydrous ethyl ether and HPLC grade chloroform were purchased from EMD Millipore (Darmstadt, Germany). Dulbecco's phosphate-buffered saline (PBS) was purchased from Thermo Fisher Scientific (Waltham, Mass.), deuterated chloroform with 1% v/v tetramethylsilane ($CDCl_3$) was purchased from Cambridge Isotope Laboratories, Inc. (Andover, Mass.), and Irgacure 819 was purchased from Ciba Specialty Chemicals Corporation (Tarrytown, N.Y.). All materials were used as received unless otherwise noted.

Example 1: Screening Synthesis and Characterization of PDFs and PDFSs

Figure 2B:
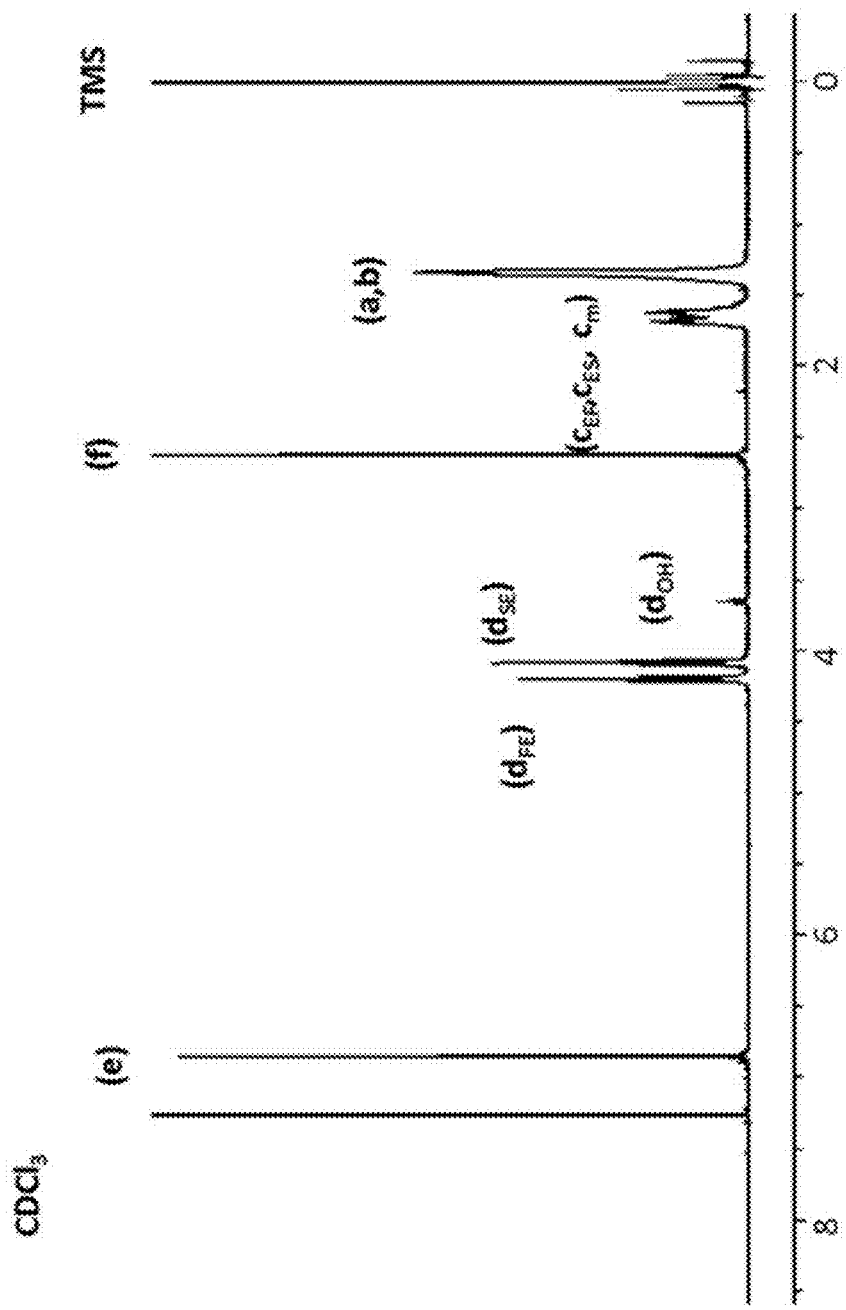
FIG. 2B provides a representative $^1$H-NMR spectrum of poly(octanediol fumarate-co-succinate). CDCl$_3$=chloroform. TMS=tetramethylsilane. Peaks drE, dsE, and dm correspond to the hydrogen adjacent to the alcohol group in fumaric ester bond, succinic ester bond, and free alcohol group, respectively.

Poly(octanediol fumarate co-succinate) and poly(decanediol fumarate co-succinate) were independently synthesized by combining the terminal diol with a 1:1 feed of fumaric acid:succinic acid. The reactions were carried out by Fisher esterification wherein equimolar concentrations of terminal diol and dicarboxylic acids were heated together at high temperature (120° C.) for 24, 48 or 72 hours under a nitrogen atmosphere for the condensation and polymerization to occur. The structure of the poly(octanediol fumarate co-succinate) is shown in FIG. 2A. Synthesis was confirmed by $^1$H NMR spectroscopy as shown in FIG. 2B which shows the spectrogram for poly(octanediol fumarate-co-succinate) synthesized for 24 hours at 120° C. in the presence of 1 mol % p-toluene sulfonic acid (PTSA). FE=fumaric ester and SE=succinic ester. The ratio of fumarate to succinate was calculated as the ratio of peak heights $P_{FE}$:$P_{SE}$ to determine the polymer FA:SA ratios as shown in Table 1, which shows the relationship between duration of reaction and polymer FA:SA ratio. In the example summarized in Table 1, the polymer is poly(decanediol fumarate-co-succinate) with a monomer feed of 1:1 FA:SA, heated at 120° C. for 24, 48, or 72 hours, without any addition of PTSA. The results show that succinic acid appears to react faster than fumaric acid in the polycondensation reaction. As the reaction progressed longer, the amount of fumaric acid moieties incorporated into the polymer increased, approaching the expected 1:1 ratio with succinic acid incorporation.

TABLE 1

| Duration of Reaction | Polymer FA:SA Ratio |
|---|---|
| 24 hr | 1:3.9 |
| 48 hr | 1:1.7 |
| 72 hr | 1:1.2 |

Example 2: Detailed Synthesis of PDFs and PDFSs

To demonstrate the variety of PDFs that can be created using the same methods, PDFs were synthesized with one of hexanediol, octanediol, or decanediol and with ratios of FA:SA monomer feed at 1:0, 1:1, and 1:2. All polymers were prepared by reacting the monomers for 24 hours at 120° C. in the presence of 1 mol % PTSA.

Figure 8:
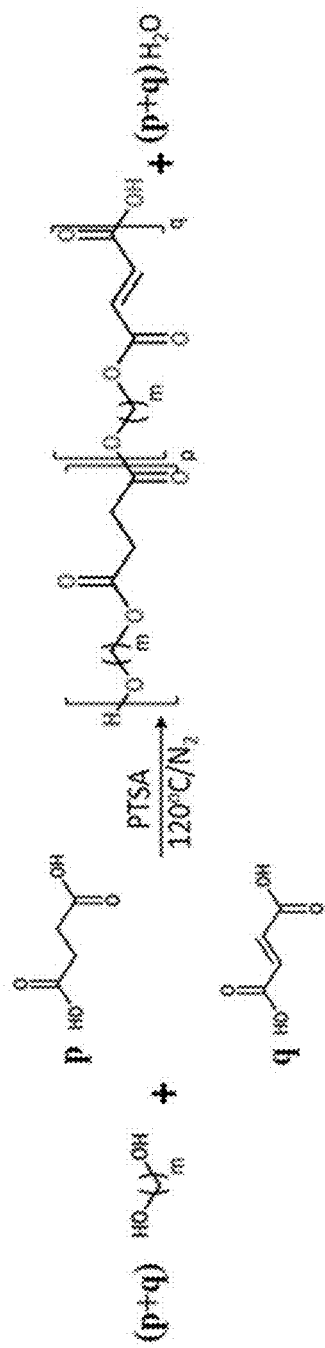
FIG. 8 depicts the reaction scheme for Fisher esterification to yield diol-based macromers. Bolded letters (p and q) represent stoichiometric coefficients.

Diol-based macromers were synthesized by Fisher esterification (Scheme 1 in FIG. 8). Briefly, equimolar concentrations of terminal diol and carboxylic acid, or mixtures of carboxylic acids at the assigned ratios, with 1 mol % PTSA were stirred at 120° C. under a nitrogen atmosphere for 24 hours. The raw product of this synthesis was then purified by phase separation and ether precipitation. Raw macromer was dissolved in an excess of chloroform (1:20 w/v) to produce an organic phase. This organic phase was placed in a separatory funnel, mixed with an excess of Millipore water (1:2 v/v), and vigorously shaken to remove unreacted dicarboxylic acids (as well as unreacted water-soluble diols and synthesized low molecular weight chains). The organic phase was isolated and then rotary evaporated to recover the remaining macromer and unreacted organic-soluble diols. This powder was re-dissolved in chloroform (1:5 w/v) and added dropwise to an excess of chilled ethyl ether (1:200 v/v). The purified macromer precipitated out of the ether and was recovered by vacuum filtration with a Grade 50 Whatman® filter (Sigma-Aldrich). The purified macromer was vacuum dried and stored at ambient temperature while shielded from light. The resulting purified products were opaque white powders of fine grain size. The final yield ranged from 17.9 to 61.5%, with P10F33 and P10F100 having lowest and highest yield, respectively.

The resulting polymer yields, FA:SA ratios and percentage of FA out of the total dicarboxylic acid content are summarized in Table 2.

TABLE 2

| Designation | Polymer | Diol | Diol Carbon Number | Monomer FA:SA Feed Ratio | % Yield | Polymer FA:SA Ratio | % FA |
|---|---|---|---|---|---|---|---|
| P6F100 | Poly(hexanediol fumarate) | Hexanediol | 6 | 1:0 | 33.7 | 1:0 | 100 |
| P6F50 | Poly(hexanediol fumarate-co-succinate) 1:1 | Hexanediol | 6 | 1:1 | 27.0 | 1:0.8 | 55.6 |
| P6F33 | Poly(hexanediol fumarate-co-succinate) 1:2 | Hexanediol | 6 | 1:2 | 35.1 | 1:1.6 | 38.5 |
| P8F100 | Poly(octanediol fumarate) | Octanediol | 8 | 1:0 | 47.3 | 1:0 | 100 |

TABLE 2-continued

| Designation | Polymer | Diol | Diol Carbon Number | Monomer FA:SA Feed Ratio | % Yield | Polymer FA:SA Ratio | % FA |
|---|---|---|---|---|---|---|---|
| P8F50 | Poly(octanediol fumarate-co-succinate) 1:1 | Octanediol | 8 | 1:1 | 25.7 | 1:1.1 | 47.6 |
| P8F33 | Poly(octanediol fumarate-co-succinate) 1:2 | Octanediol | 8 | 1:2 | 8.3 | 1:2.6 | 27.0 |
| P10F100 | Poly(decanediol fumarate) | Decanediol | 10 | 1:0 | 61.5 | 1:0 | 100 |
| P10F50 | Poly(decanediol fumarate-co-succinate) 1:1 | Decanediol | 10 | 1:1 | 26.8 | 1:0 | 50.0 |
| P10F33 | Poly(decanediol fumarate-co-succinate) 1:2 | Decanediol | 10 | 1:2 | 17.9 | 1:2.6 | 27.8 |

Proton Nuclear Magnetic Resonance ($^1$H NMR) Spectroscopy

Purified macromer was dissolved in CDCl$_3$ (about 10 mg/mL) and subjected to $^1$H NMR spectroscopy utilizing a 400 MHz spectrometer (Bruker, Switzerland) and analyzed with TOPSPIN 3.0 software (Bruker). To determine the actual amount of FA among dicarboxylic acid groups in the final macromer backbone, integration of the spectrum was performed at 4.13-4.23 ppm and 4.02-4.12 ppm (attributed to protons adjacent to the fumarate ester bond and succinic acid ester bond, respectively). Macromer amount of FA (mol %) was calculated as described in Equation 1.

$$\text{Macromer Amount of } FA = \frac{Area_{4.13-4.23ppm}}{Area_{4.13-4.23ppm} + Area_{4.02-4.12ppm}} \times 100\% \quad \text{(Eq. 1)}$$

Figure 9:
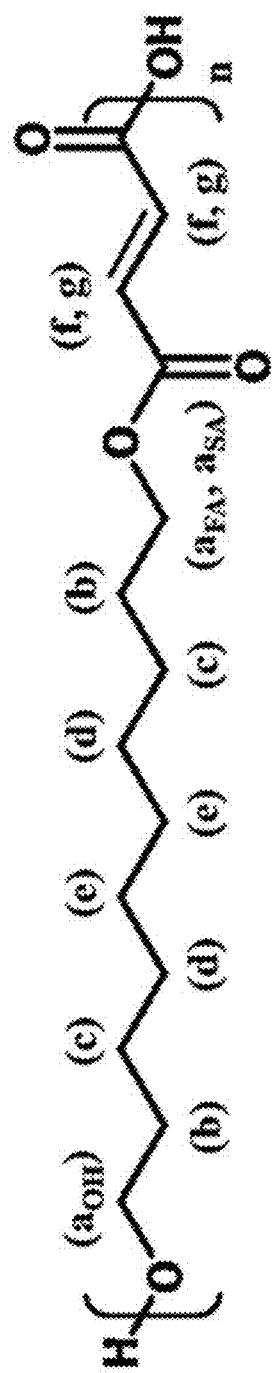
FIG. 9 depicts a representative macromer (P10F50) with the hydrogens corresponding to the labeled peaks in FIG. 10A labeled with letters. Red indicates hydrogens and bonds specific to fumaric acid.
Figure 10B:
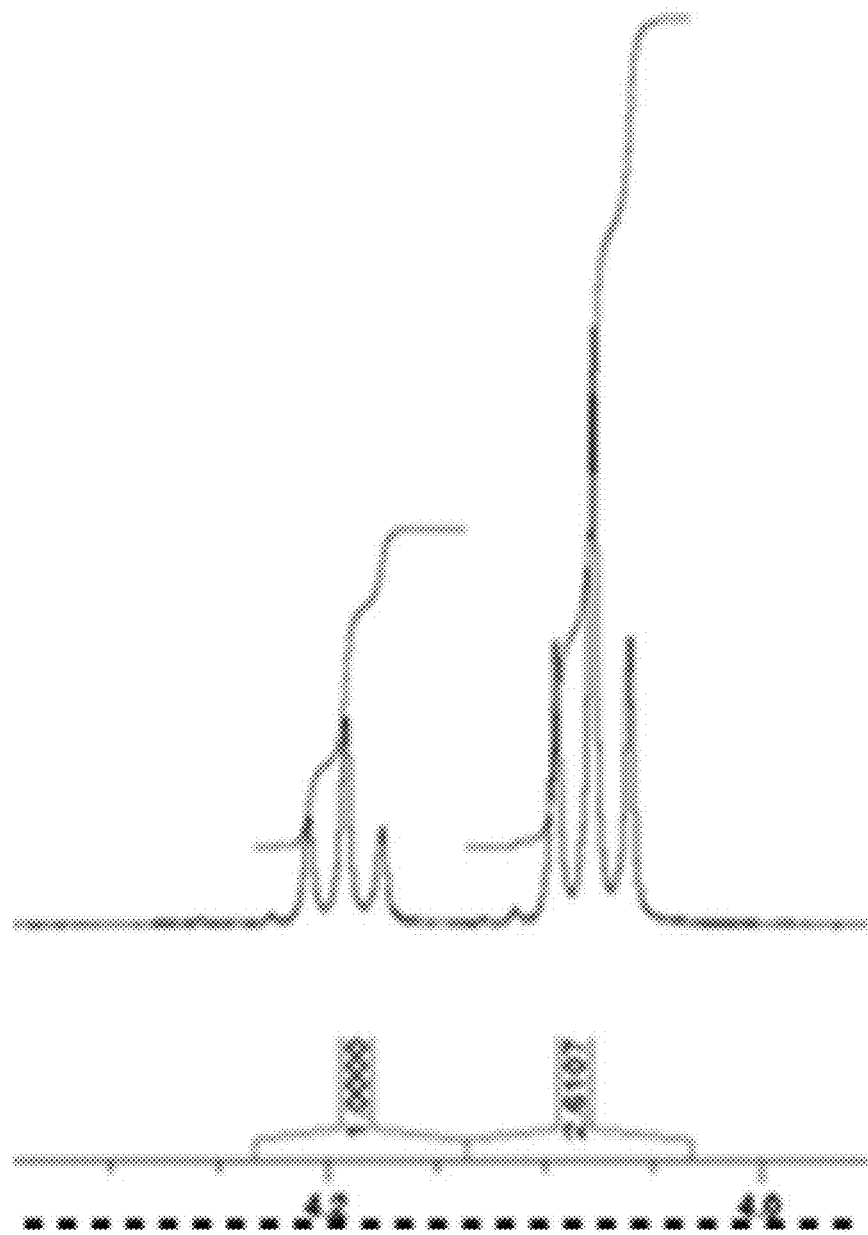
FIG. 10B shows a magnified region of P10F33 $^1$H NMR (CDCl$_3$ with 1% v/v TMS, 400 MHz): δ 4.08 (t, 4H, J=7.1 Hz), 4.19 (t, 4H, J=7.1 Hz).
Figure 10C:
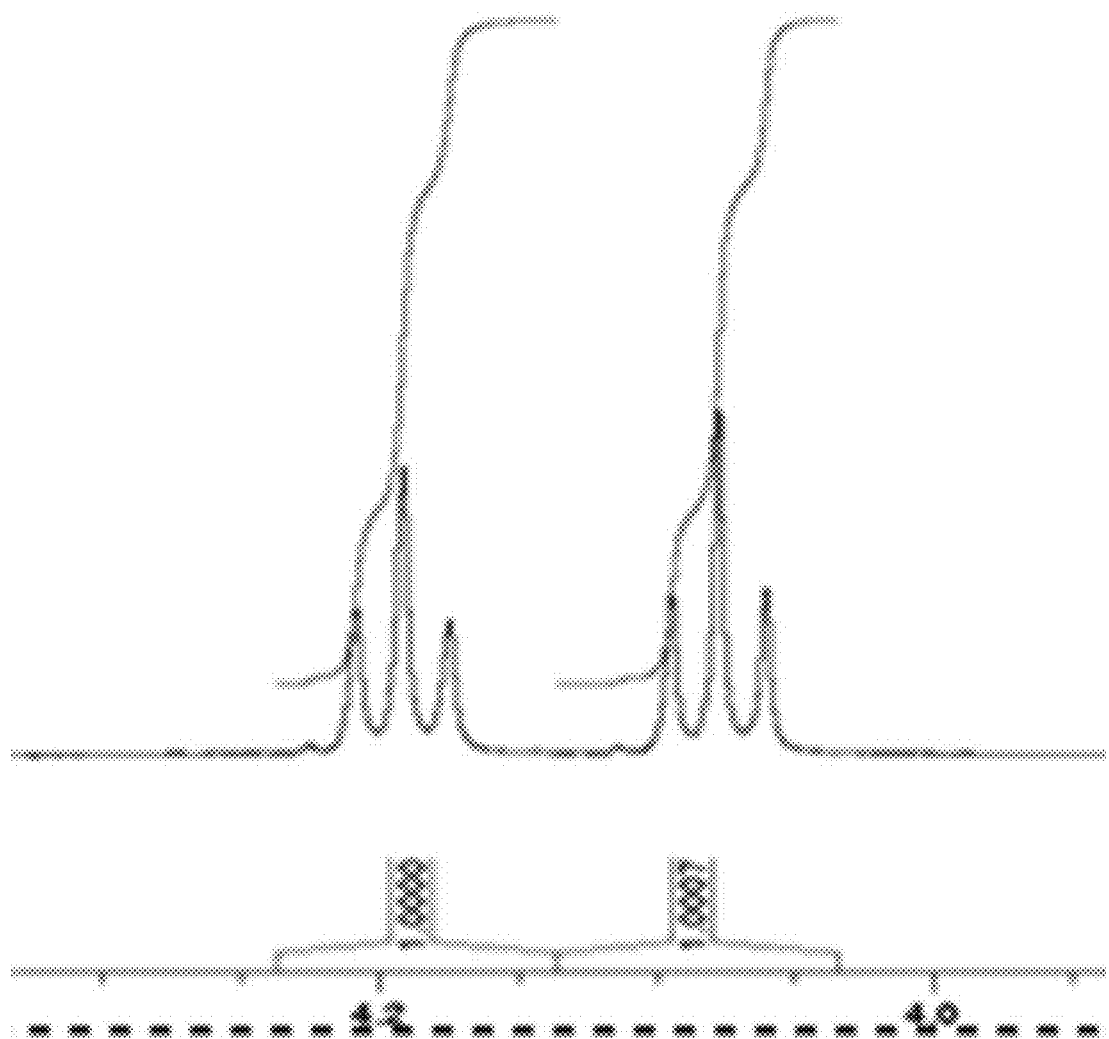
FIG. 10C shows a magnified region of P10F50 $^1$H NMR (CDCl$_3$ with 1% v/v TMS, 400 MHz): δ 4.08 (t, 4H, J=7.2 Hz), 4.19 (t, 4H, J=7.2 Hz).
Figure 10D:
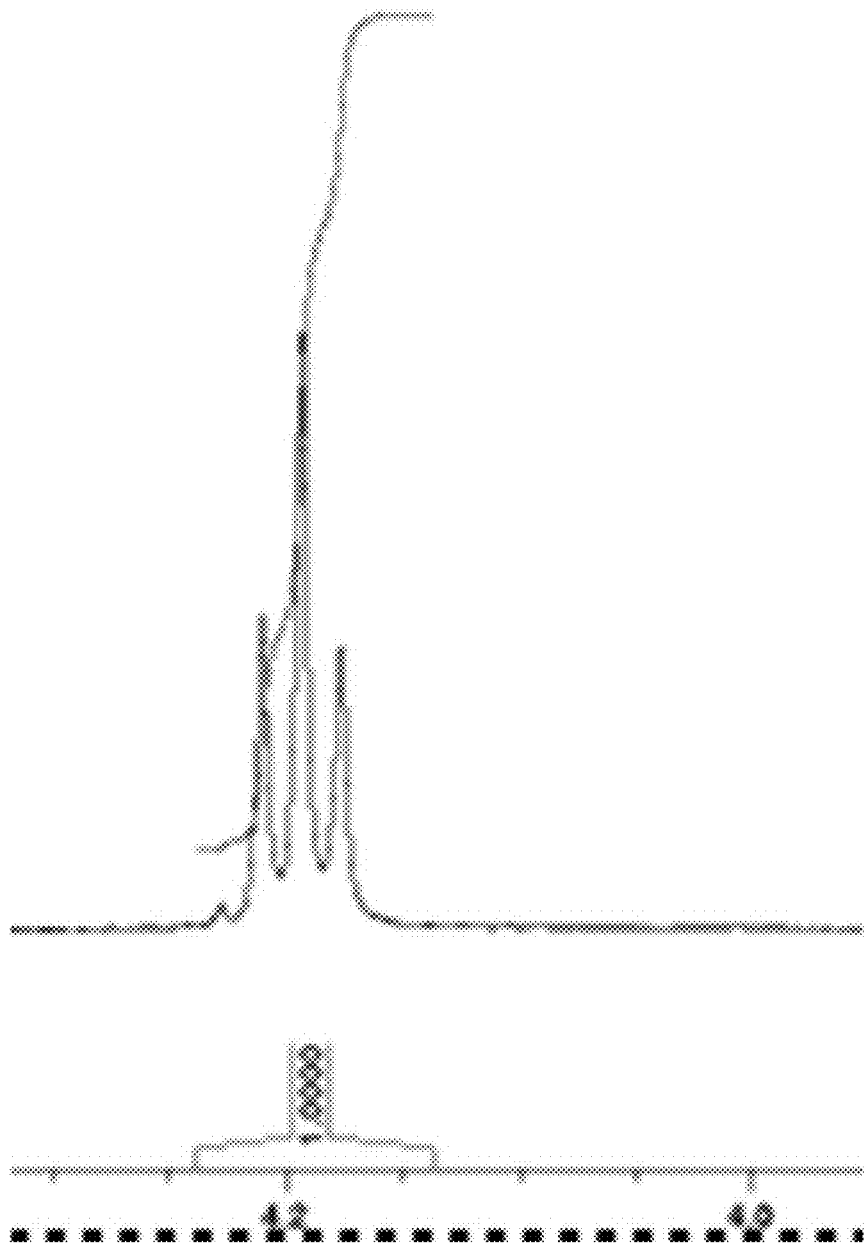
FIG. 10D shows a magnified region of P10F100 $^1$H NMR (CDCl$_3$ with 1% v/v TMS, 400 MHz): δ 4.19 (t, 4H, J=6.9 Hz).

A representative spectrum (taken from P10F50, structure shown in FIG. 9) is shown in FIG. 10A. As the amount of FA increased in the dicarboxylic acid monomer feed, the resulting integrated area under those respective ester peaks also changed to reflect the relative amounts of FA and SA in the final macromer backbone (FIGS. 10B-10D). A comparison between the initial amount of FA monomer feed versus the final amount of FA incorporated macromer backbone is given in Table 2. The 1,6-hexanediol-based groups had a higher final amount of FA in the macromer compared with monomer feed at both the 33% and 50% levels than the other diols. Both the 1,8-octanediol- and 1,10-decanediol-based groups had nearly the same amount of FA between monomer feed and macromer backbone at the 50% level and a decreased amount of FA (27.0 and 27.8%) at the 33% monomer feed level.

In the polymers, the ratio of fumaric acid to succinic acid is from 1:0.6 to 1:4, or from 1:0.8 to 1:4, or from 1:06 to 1.3, preferably from 1:0.8 to 1:3. In the polymers, the ratio of fumaric acid to succinic acid may also be from 1:0 to 1:0.8. The polymers comprise at least 25 mol % of fumaric acid units based on the total molar amount of dicarboxylic acid units, such as from 25 mol % to 50 mol %, or from 25 mol % to 60 mol %, or from 25 mol % to 75 mol %, or from 25 mol % to 100 mol %, or from 50 mol % to 75%, or from 50 mol % to 100 mol %, or from 60 mol % to 100 mol %.

The results confirm esterification as demonstrated by a downfield shift in the CH$_2$—OR (R=H, CO) protons from 3.65 ppm to either 4.1 ppm (succinic ester) or 4.20 ppm (fumaric ester).

Diols and dicarboxylic acids can only form co-polymers (they cannot react with themselves to form polymers). Therefore, the final macromer chain is a statistical alternating co-polymer for P6F100, P8F100, and P10F100. When mixtures of dicarboxylic acids are used, the polyester comprises alternating diol and diacid moieties. As can be seen from Table 2, the charged monomer amount of FA did not always correspond to the final amount of FA within the macromer chain backbone. For example, P10F33 had a 33 mol % amount of FA per its total dicarboxylic acid monomer feed, yet its final backbone had incorporated only 28 mol % amount of FA (Table 2). This decrease in the amount of FA between monomer to macromer was also observed in P8F33. At a molecular level, the difference between succinic acid and fumaric acid is the presence of a carbon-carbon double bond in fumaric acid versus a single bond in succinic acid. Without being held to any particular hypothesis, the presence of a π bond in fumaric acid may add stability to the fumaric cation compared to the succinic cation. Therefore, esterification of succinic acid may be more energetically favorable than esterification of fumaric acid. If there are differences in the reactivity of the two dicarboxyclic acids, this competitive reaction would be expected to result in a disparity between monomer feed ratio and final macromer backbone due to selective succinic acid incorporation. This was also demonstrated by the results summarized in Table 1, in which succinic acid was incorporated at a faster rate than fumaric acid in the early phases of the polymerization. At 50 mol % amount of FA, there is a 1:1 ratio of FA:SA monomer available for reaction and the effect of this competitive interaction may be less pronounced as there are more available diols proportional to fumaric acid. This also suggests that the resulting polymers may be somewhat blocky, with succinic acid-rich regions, compared to a strictly random distribution of succinate and fumarate along the polymer chain. Longer reaction times may lead to polymers with FA:SA ratios more equal to the feed ratio and a more random distribution.

Figure 3:
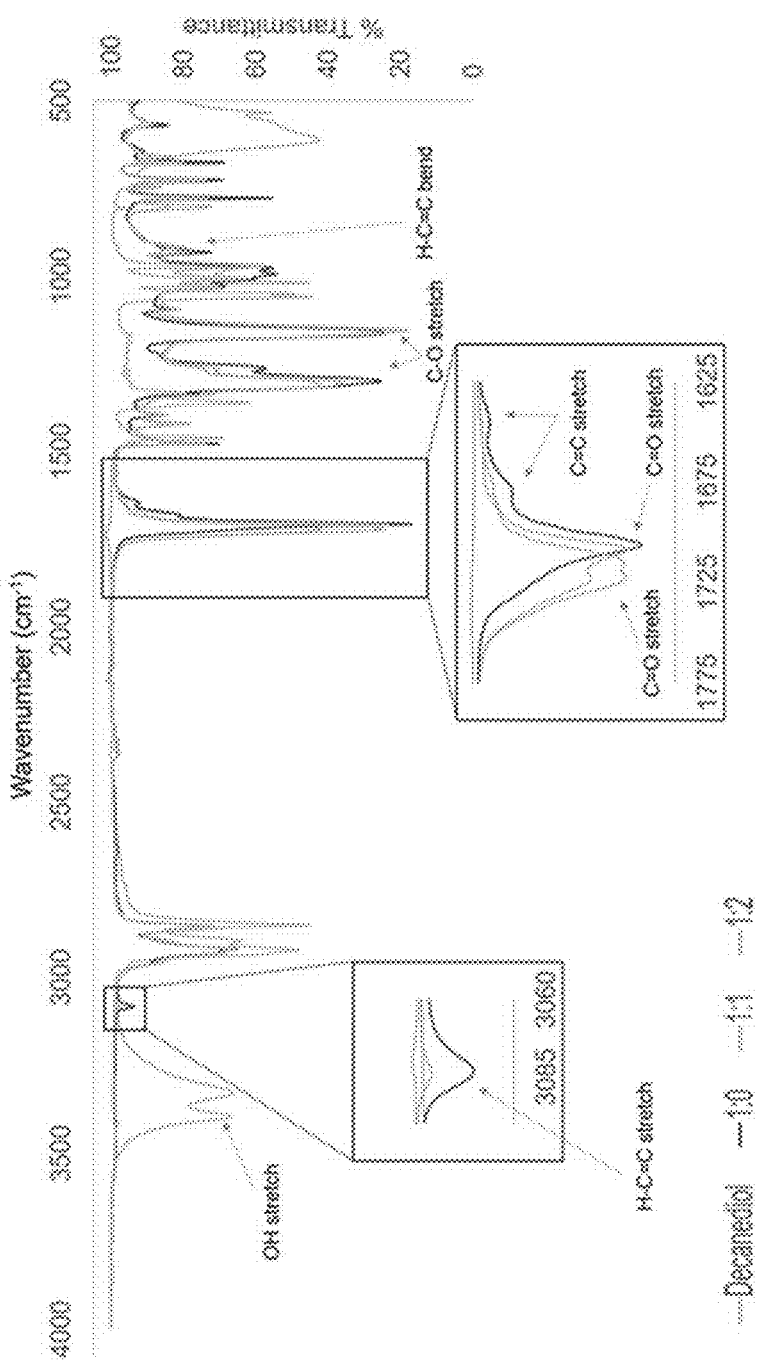
FIG. 3 depicts the relationship between FA:SA ratio and % transmittance. In this example, the decanediol-based polymers with a FA:SA monomer feed of 1:0, 1:1, and 1:2 are compared with each other and unmodified decandiol as control (grey).

PDFs from Table 2 were analyzed by FTIR as shown in FIG. 3. As FA decreases and SA increases, there is a decrease in unsaturated C=C—H stretch (3082 cm$^{-1}$), C=C stretch (1641 and 1677 cm$^{-1}$), and C=C—H bend (~915 cm$^{-1}$). One can also observe shifts in the ester bonds as the succinic ester (1722 cm$^{-1}$) and fumaric ester (1705 cm$^{-1}$) have different peaks due to resonance structure. These FTIR data further demonstrate our ability to successfully synthesize a wide variety of PDFs and PDFSs with various tunable chemical properties.

Figure 4:
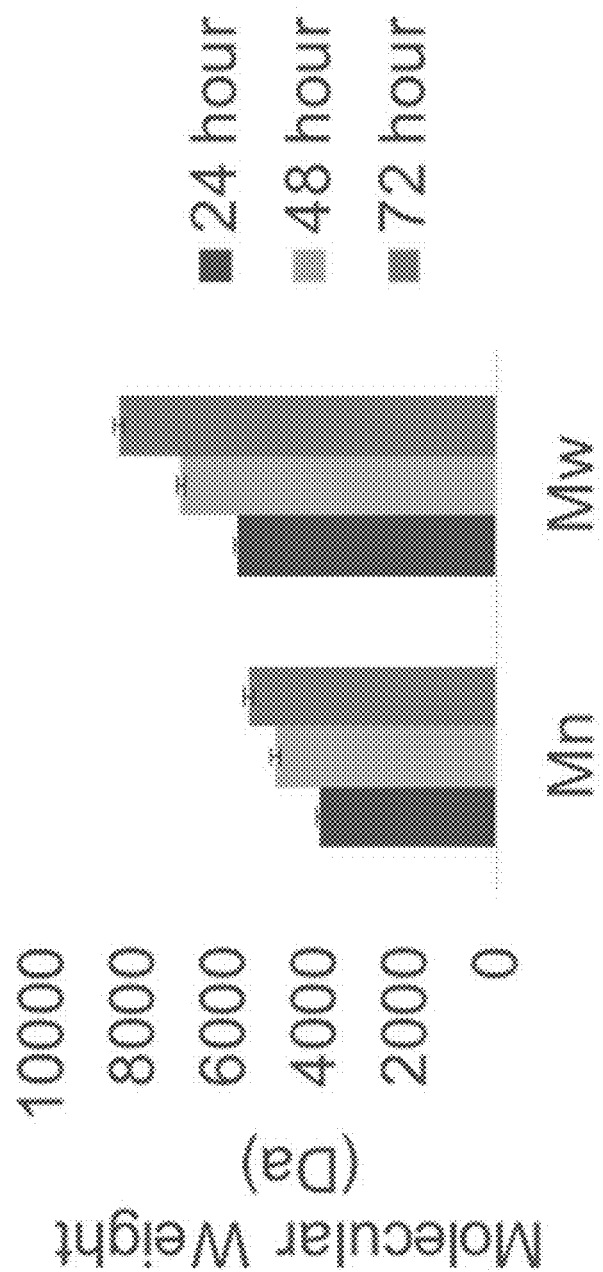
FIG. 4 is a bar graph demonstrating the relationship between duration of reaction and chain length. In this example, the polymer is poly(decanediol fumarate-cosuccinate) with a monomer feed of 1:1 FA:SA, heated at 120° C. for 24, 48, or 72 hours, without any addition of PTSA (n=3). Mn=number average molecular weight; Mw=weight average molecular weight. $p<0.05$ between all time points.
Figure 5B:
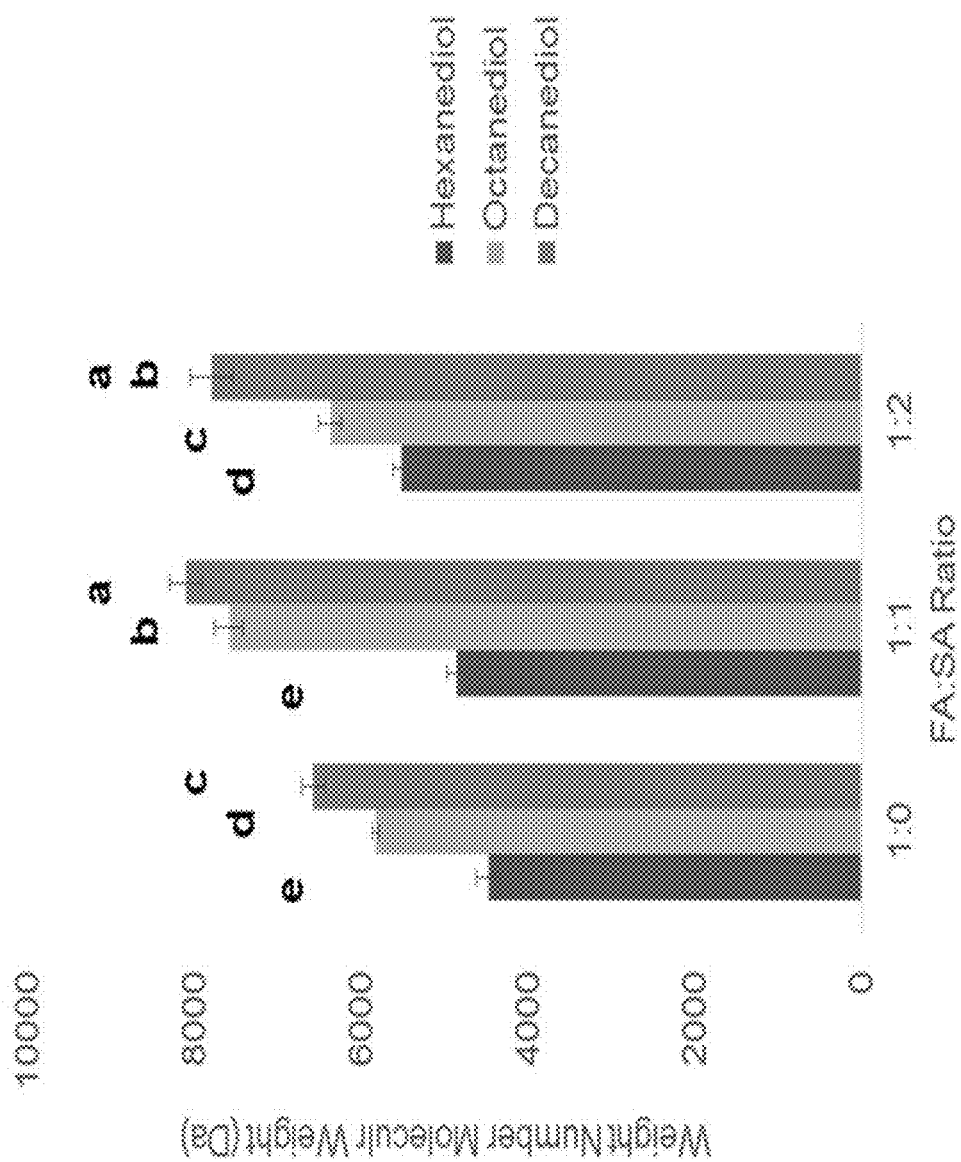
FIG. 5B is a bar graph demonstrating the relationship between diol and FA:SA ratio on weight average molecular weight (n=3) of PDFs synthesized for 24 hr at 120° C. in the presence of 1 mol % PTSA. Those that do not share a letter are significantly different ($p<0.05$).

Gel Permeation Chromatography (GPC) was used to determine the chain length (molecular weight) of the PDFs and PDFSs. Briefly, purified polymers are dissolved in chloroform (1:100 w/v) and filtered by injection through a 0.45 μm filter. We used a Waters GPC system with a chloroform mobile phase at a flow rate of 1 mL/min and temperature of 30° C. with a Waters HR2 column and polystyrene standards. Using these methods, the effect of different parameters such as duration of reaction, diol, and FA:SA ratio on polymer chain length were studied. For example, increasing the duration of reaction significantly increased the molecular weight of poly(decanediol fumarate-co-succinate) (1:1) (FIG. 4). All nine variations of PDFs and PDFSs listed in Table 2 were examined by GPC (FIGS. 5A-5B).

Figure 6A:
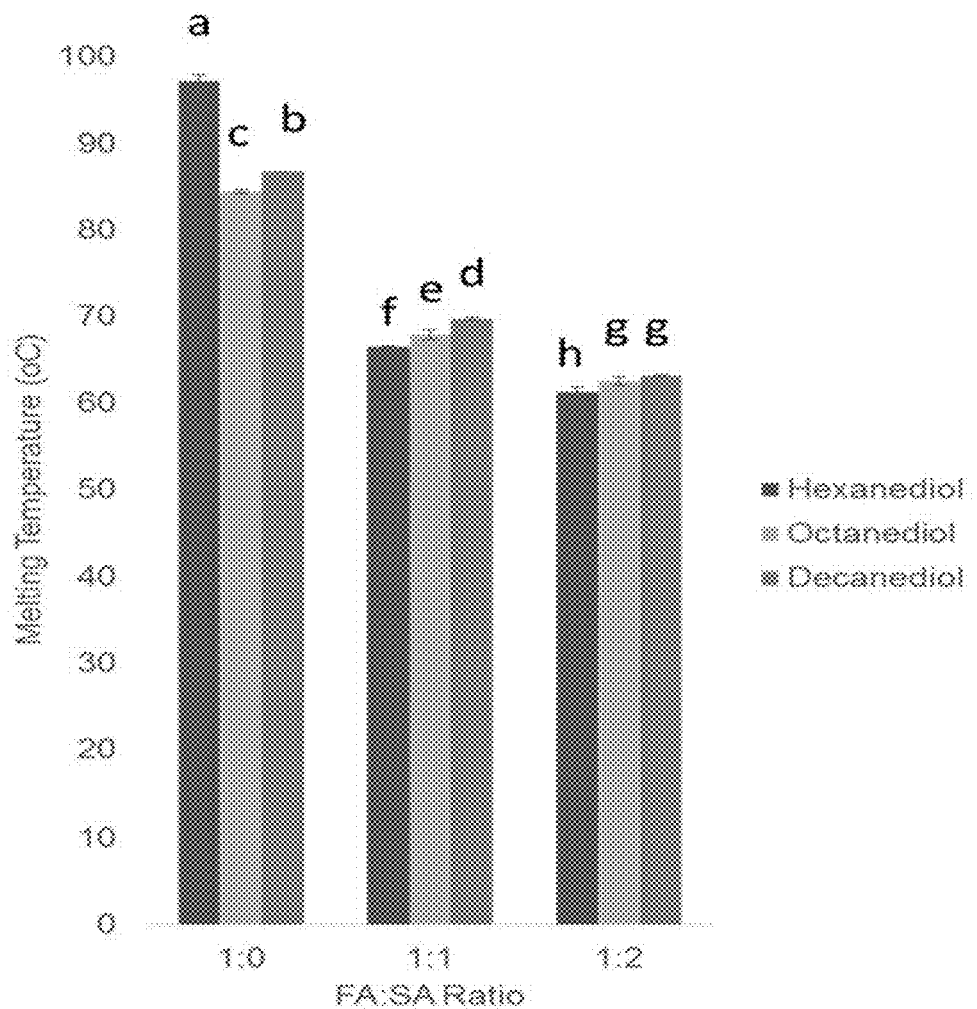
FIG. 6A is a bar graph demonstrating the relationship between diol and FA:SA ratio on melting temperatures (n=3) of polymers synthesized for 24 hr at 120° C. in the presence of 1 mol % PTSA. Those that do not share a letter are significantly different ($p<0.05$).
Figure 6B:
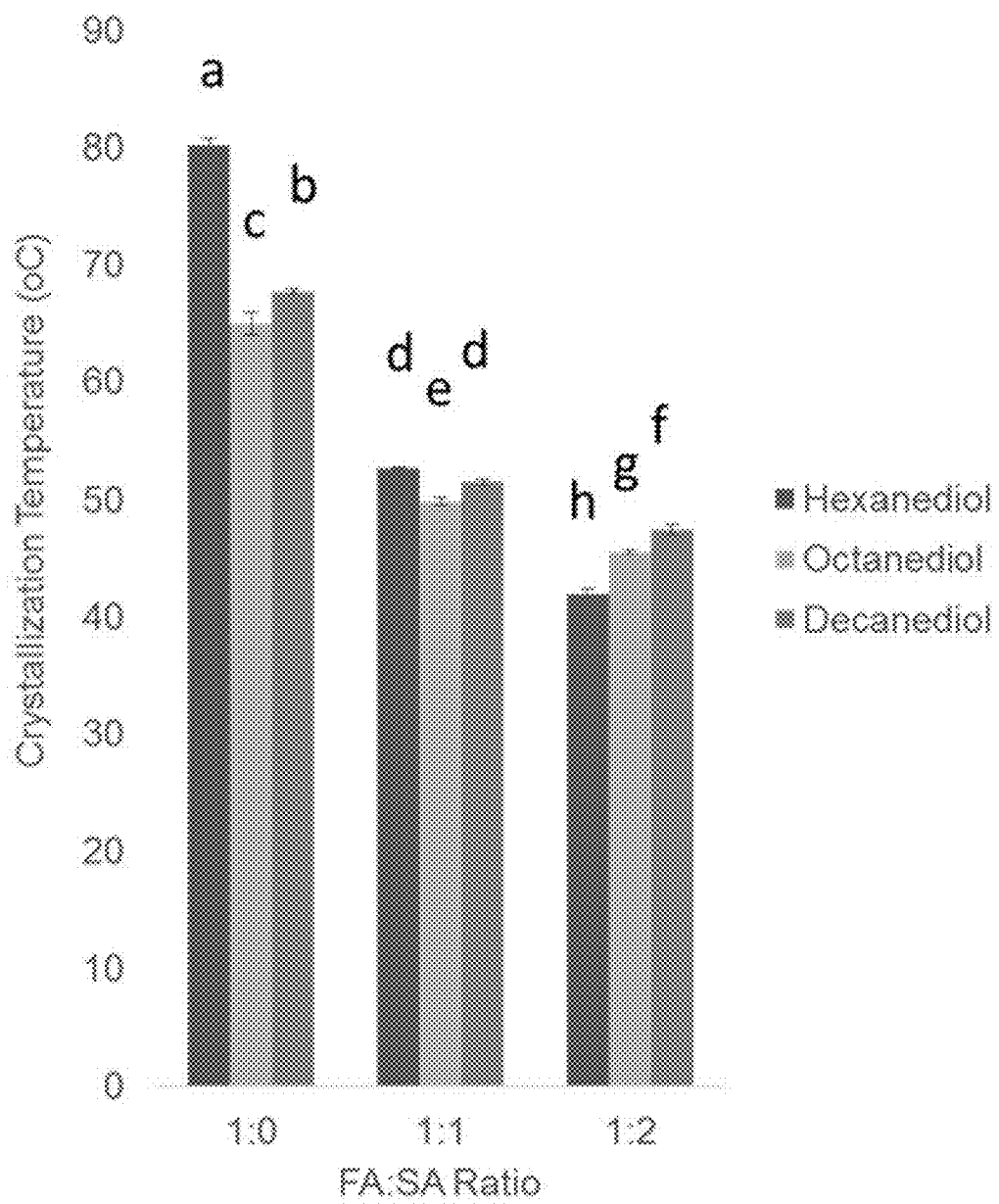
FIG. 6B is a bar graph demonstrating the relationship between diol and FA:SA ratio on crystallization temperatures (n=3) of polymers synthesized for 24 hr at 120° C. in the presence of 1 mol % PTSA. Those that do not share a letter are significantly different ($p<0.05$).

Differential Scanning calorimetry (DSC) was utilized to determine the thermal properties (melting temperature, crystallization temperature, glass transition temperature) of the PDFs and PDFSs. Briefly, 1.5-3 mg of purified polymer was added to aluminum pans. The pans were heated at 5° C./min between −70° C. and 120° C. for two cycles (starting at ambient temperature) in a TA Instruments differential scanning calorimeter. Using these methods, the effect of different parameters such as duration of reaction, diol, and FA:SA ratio on polymer chain length was studied. For example, increasing the amount of succinic acid decreases the melting and crystallization temperatures of PDFs and PDFSs (FIGS. 6A-6B). All nine variations of PDFs and PDFSs evaluated in Table 2 were examined by DSC. Interestingly, none of these variants demonstrated a glass transition temperature, suggesting that they are primarily crystalline rather than amorphous in structure.

Analysis of Synthesized Diol-Based Macromers

The effects of diol carbon number and amount of FA on macromer chain length and thermal properties were examined. In addition, after these macromers were covalently crosslinked into networks, the effects of diol carbon number and amount of FA on network sol fraction, swelling, and compressive modulus were examined.

Size Exclusion Chromatography (SEC)

SEC was performed to determine chain length using a Waters (Milford, Mass.) gel permeation chomatography system, consisting of pump (Waters Model No. 155), injection module (Waters No. 717), and refractive index detector (Waters Model No. 410) per established methods. Purified polymer was dissolved in chloroform (15 mg/mL) and filtered through a 0.45 μm Whatman injection filter. SEC was performed (n=3 of technical replicates per synthesis in Table 3) at a flow rate of 1 mL/min and a temperature of 30° C. with a Styragel® HR2 THF 5 μm, 7.8 mm×300 mm column (Waters) with Styragel® 20 μm, 4.6 mm×30 mm guard column. A calibration curve was constructed using linear polystyrene standards with peak molecular weights ranging from 1.1 kDa to 32.5 kDa. The number average molecular weight ($M_n$), weight average molecular weight ($M_w$), and polydispersity index (PI) were measured and calculated using the software Empower (Waters). The number average number of repeating units ($RU_n$) and weight average number of repeating units ($RU_w$), representing the number of repeating units per chain, were calculated by normalizing the Mn and $M_w$ by the molecular weight of a single repeating unit, taking into consideration the specific diol/dicarboxylic acid molecular weight and proportions used in each synthesis. Lastly, the number average number of unsaturated bonds ($B_n$) and weight average number of unsaturated bonds ($B_w$), representing the available carbon-carbon double bonds per chain, were calculated by multiplying the number of repeating units by the amount of FA (mol %) present in the macromer backbone.

Figure 11A:
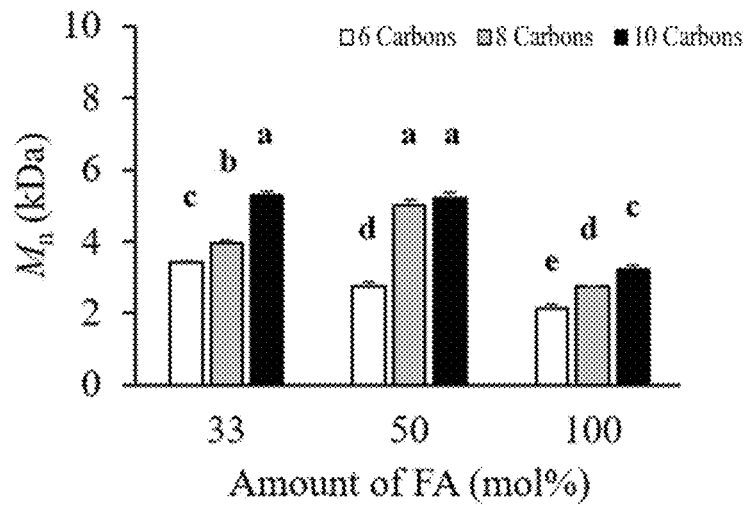
FIG. 11A shows the results from size exclusion chromatography for the number average molecular weight for different macromers. Error bars represent standard deviation. Those that do not share the same letter are significantly different ($p<0.05$).
Figure 11B:
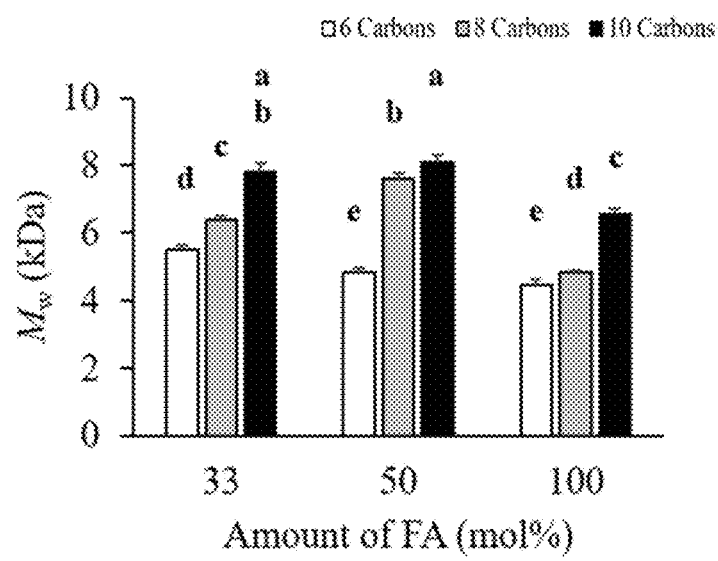
FIG. 11B shows the results from size exclusion chromatography for the weight average molecular weight for different macromers. Error bars represent standard deviation. Those that do not share the same letter are significantly different ($p<0.05$).
Figure 11C:
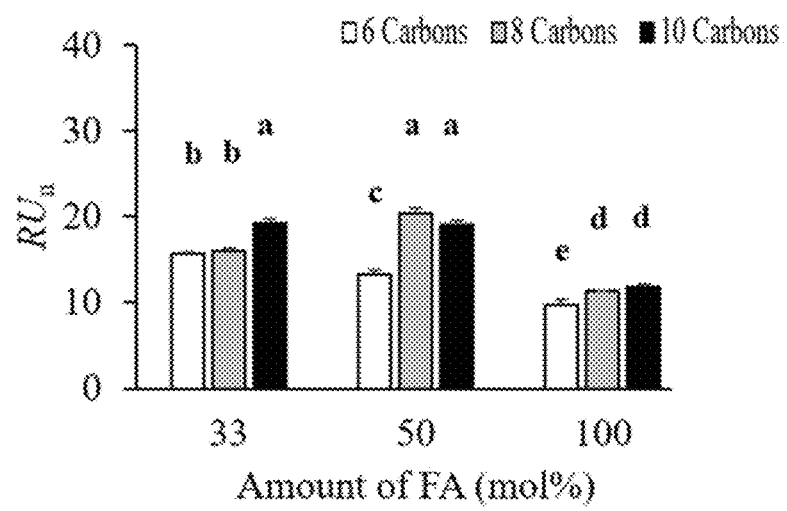
FIG. 11C shows the results from size exclusion chromatography for the number average repeating units for different macromers. Error bars represent standard deviation. Those that do not share the same letter are significantly different (p<0.05).
Figure 11D:
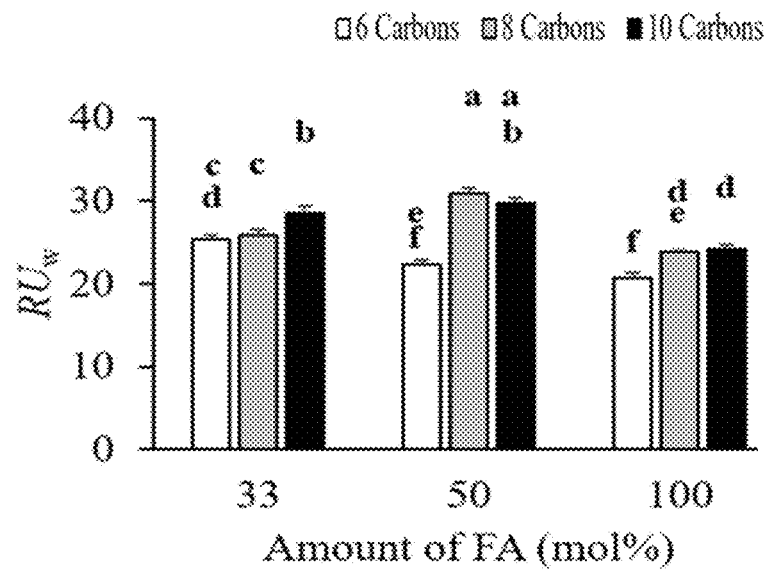
FIG. 11D shows the results from size exclusion chromatography for the weight average repeating units for different macromers. Error bars represent standard deviation. Those that do not share the same letter are significantly different (p<0.05).
Figure 11E:
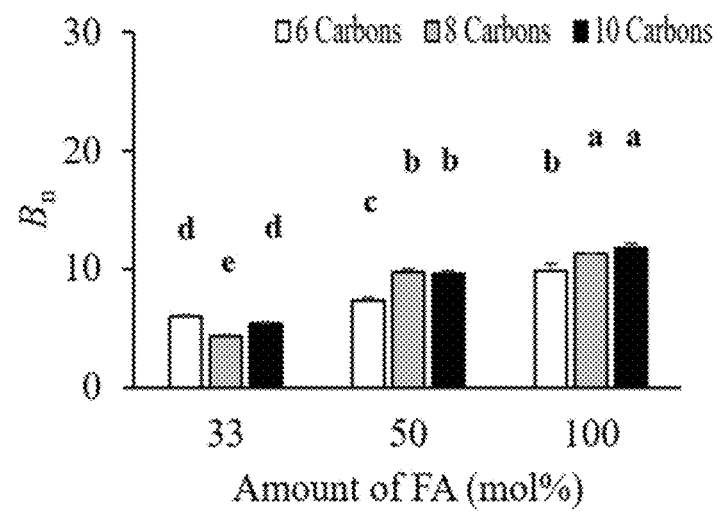
FIG. 11E shows the results from size exclusion chromatography for the number average unsaturated bonds per chain for different macromers. Error bars represent standard deviation. Those that do not share the same letter are significantly different (p<0.05).
Figure 11F:
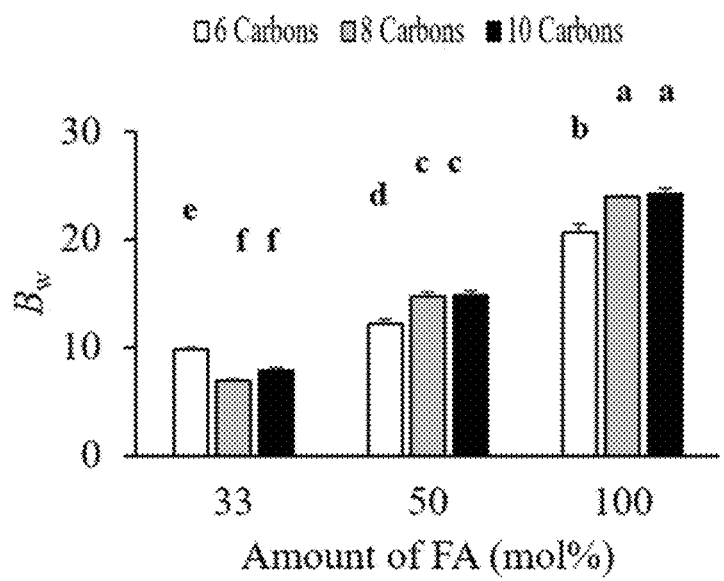
FIG. 11F shows the results from size exclusion chromatography for the weight average unsaturated bonds per chain for different macromers. Error bars represent standard deviation. Those that do not share the same letter are significantly different (p<0.05).

By SEC, the macromer Mn ranged from 2.12±0.13 to 5.27±0.13 kDa (P6F100 and P10F33, respectively) and $M_w$ ranged from 4.47 kDa±0.15 to 8.10±0.19 kDa (P6F100 and P10F50, respectively) (Table 3 and FIGS. 11A-11B). In general, greater diol carbon number and decreased amount of FA resulted in macromer chains with greater molecular weight. These trends held true for the number of repeating units per chain, a measurement that normalized the molecular weight by the weight of the particular diols (FIGS. 11C-11D). $RU_n$ ranged from 9.8±0.6 to 20.3±0.7 repeating units/chain (P6F100 and P8F50, respectively) and $RU_w$ ranged from 20.7±0.7 to 30.9±0.7 repeating units/chain (P6F100 and P8F50, respectively). The number of unsaturated bonds per chain increased with increasing diol carbon number and increasing amount of FA in the monomer feed (FIGS. 11E-11F). $B_n$ ranged from 4.3±0.1 to 11.8±0.4 unsaturated bonds/chain (P8F33 and P10F100, respectively) and $B_w$ ranged from 7.0±0.2 to 24.1±0.5 unsaturated bonds/chain (P8F33 and P10F100, respectively). PI ranged from 1.48±0.02 to 2.11±0.07 (P10F33 and P6F100 respectively), decreased with increasing diol carbon number, and increased with increasing amount of FA (Table 3). Values are reported as mean±standard deviation. Within the same column, those that do not share the same letter are significantly different (p<0.05).

TABLE 3

| Macromer | $M_n$ (kDa) | $M_w$ (kDa) | PI | $RU_n$ | $RU_w$ | $B_n$ | $B_w$ | $T_m$ (° C.) | $T_c$ (° C.) |
|---|---|---|---|---|---|---|---|---|---|
| P6F33 | 3.40 ± 0.05$^e$ | 5.51 ± 0.10$^d$ | 1.62 ± 0.01$^{b,c}$ | 15.6 ± 0.2$^b$ | 25.4 ± 0.5$^{c,d}$ | 6.0 ± 0.1$^d$ | 9.8 ± 0.2$^e$ | 61.2 ± 0.7$^h$ | 42.0 ± 0.4$^h$ |
| P6F50 | 2.76 ± 0.10$^d$ | 4.85 ± 0.12$^e$ | 1.68 ± 0.02$^b$ | 13.3 ± 0.5$^c$ | 22.3 ± 0.6$^{e,f}$ | 7.3 ± 0.3$^c$ | 12.3 ± 0.3$^d$ | 66.5 ± 0.1$^f$ | 52.7 ± 0.1$^d$ |
| P6F100 | 2.12 ± 0.13$^e$ | 4.47 ± 0.15$^e$ | 2.11 ± 0.07$^a$ | 9.8 ± 0.6$^e$ | 20.7 ± 0.7$^f$ | 9.8 ± 0.6$^b$ | 20.7 ± 0.7$^b$ | 97.3 ± 0.7$^a$ | 80.2 ± 0.6$^a$ |
| P8F33 | 3.95 ± 0.07$^b$ | 6.37 ± 0.13$^c$ | 1.61 ± 0.01$^{b,c}$ | 16.1 ± 0.3$^b$ | 25.9 ± 0.6$^c$ | 4.3 ± 0.1$^e$ | 7.0 ± 0.2$^f$ | 62.6 ± 0.5$^g$ | 45.6 ± 0.2$^g$ |
| P8F50 | 4.99 ± 0.16$^a$ | 7.58 ± 0.17$^b$ | 1.52 ± 0.02$^d$ | 20.3 ± 0.7$^a$ | 30.9 ± 0.7$^a$ | 9.7 ± 0.3$^b$ | 14.7 ± 0.3$^c$ | 67.9 ± 0.6$^e$ | 49.9 ± 0.3$^e$ |
| P8F100 | 2.76 ± 0.01$^d$ | 5.83 ± 0.04$^d$ | 2.11 ± 0.02$^a$ | 11.3 ± 0.0$^d$ | 23.9 ± 0.2$^{d,e}$ | 11.3 ± 0.0$^a$ | 23.9 ± 0.2$^a$ | 84.5 ± 0.2$^c$ | 65.0 ± 1.0$^c$ |
| P10F33 | 5.27 ± 0.12$^a$ | 7.79 ± 0.26$^{a,b}$ | 1.48 ± 0.02$^d$ | 19.3 ± 0.4$^a$ | 28.5 ± 0.9$^b$ | 5.3 ± 0.1$^d$ | 7.9 ± 0.3$^f$ | 63.1 ± 0.1$^g$ | 47.5 ± 0.4$^f$ |
| P10F50 | 5.22 ± 0.13$^a$ | 8.10 ± 0.19$^a$ | 1.55 ± 0.02$^{c,d}$ | 19.1 ± 0.5$^a$ | 29.6 ± 0.7$^{a,b}$ | 9.6 ± 0.2$^b$ | 14.8 ± 0.4$^c$ | 69.8 ± 0.2$^d$ | 51.5 ± 0.3$^d$ |
| P10F100 | 3.21 ± 0.11$^c$ | 6.57 ± 0.14$^c$ | 2.05 ± 0.03$^a$ | 11.8 ± 0.4$^d$ | 24.3 ± 0.5$^d$ | 11.8 ± 0.4$^a$ | 24.1 ± 0.5$^a$ | 86.8 ± 0.0$^b$ | 67.7 ± 0.2$^b$ |

The average number of unsaturated bonds per chain was calculated for each group (FIGS. 11E-11F). Diol carbon number had no effect on unsaturated bonds per chain and increasing amount of FA significantly increased the amount of unsaturated bonds per chain (Table 5). As each additional fumarate group contains an unreacted unsaturated bond, this platform allows for control over the degree of carbon-carbon double bond density per chain.

Differential Scanning Calorimetry (DSC)

DSC was performed to determine the thermal properties of the comacromers in Table 2 per established methods.

Briefly, 1.5-3 mg of purified polymer (n=3 technical replicates per synthesis in Table 3) were added to aluminum pans (DSC Consumables, Inc., Austin, Minn.), melted for several seconds at 120° C. to maximize surface contact with the pan, and then immediately flash frozen in liquid nitrogen to promote the amorphous state. The pans were then heated at 5° C./min between −70° C. and 120° C. for two cycles (starting at ambient temperature) in a TA Instruments (New Castle, Del.) differential scanning calorimeter (Model No. 2920). Melting temperature ($T_m$), crystallization temperature ($T_c$), and glass transition temperature ($T_g$) were measured and analyzed with the software Universal Analysis 2000 (TA Instruments).

Figure 12A:
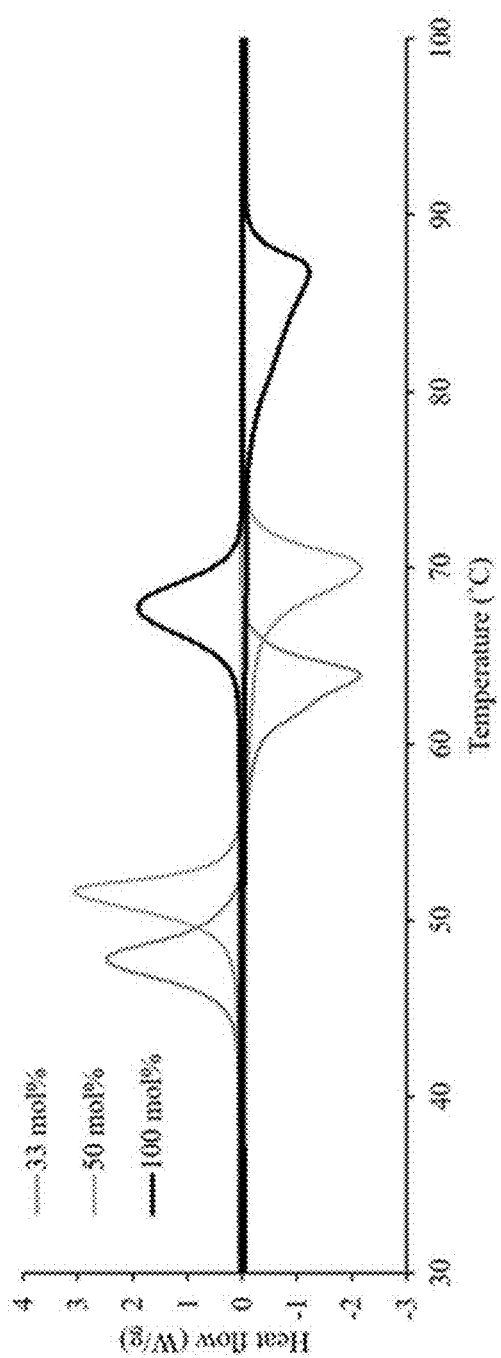
FIG. 12A shows a magnified region of representative DSC curves using decanediol-based macromers as an example. Error bars represent standard deviation. Those that do not share the same letter are significantly different (p<0.05).

No glass transition temperature points were observed within the examined temperature range (−70 to 120° C.) for any group (representative thermal curves of 1,10-decanediol-based groups are shown as examples in FIG. 12A). The melting temperature (FIG. 12B) of the diol-based macromers ranged from 61.2±0.7 to 97.3±0.7° C. (P6F33 and P6F100, respectively) and the crystallization temperature (FIG. 12C) ranged from 42.0±0.4 to 80.2±0.6° C. (P6F33 and P6F100, respectively). Both melting and crystallization temperatures significantly increased with increasing amount of FA with no significant effect of diol carbon number (Table 6).

Figure 12B:
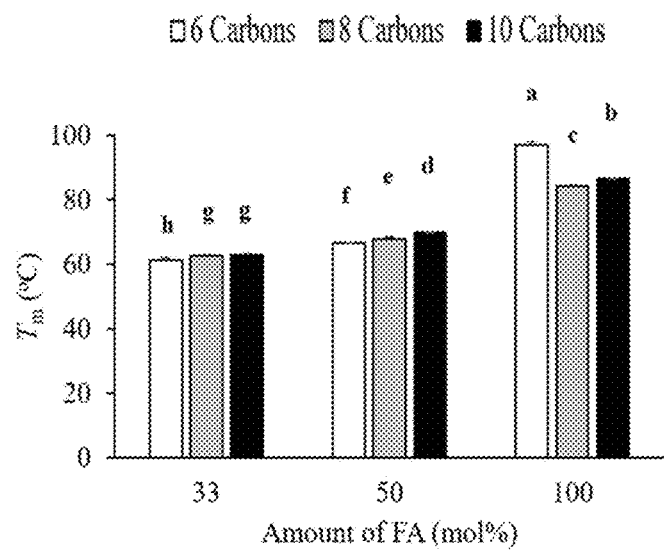
FIG. 12B shows the melting temperature for different macromers. Error bars represent standard deviation. Those that do not share the same letter are significantly different (p<0.05).
Figure 12C:
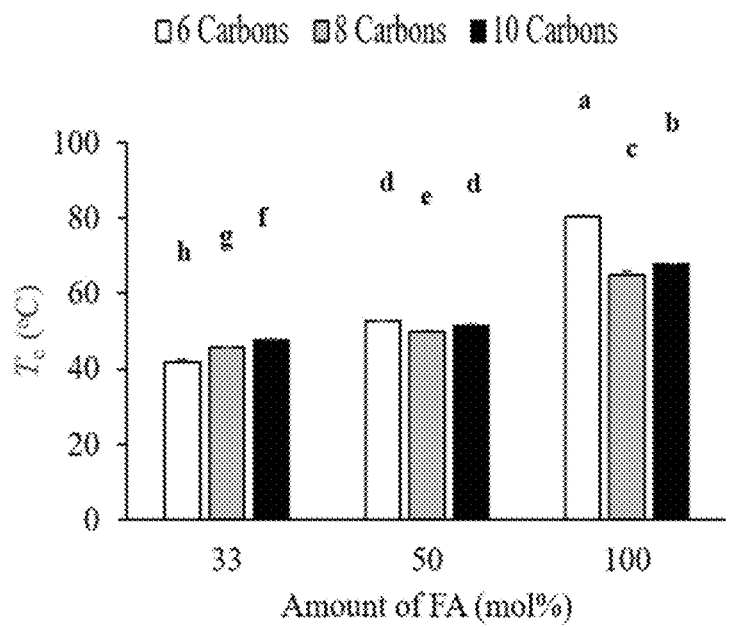
FIG. 12C shows the crystallization temperature for different macromers. Error bars represent standard deviation. Those that do not share the same letter are significantly different (p<0.05).

Macromer melting temperature reflects the packing density of molecular chains. If macromer chains are able to pack tightly, a greater degree of secondary bonds and interactions within folded single chains and between multiple chains can form. More energy is required (higher $T_m$) to break a greater amount of van der Waals interactions and unpack tightly bound chains. In this study, diol-based macromers with 100 mol % amount of FA had significantly greater melting and crystallization temperatures, regardless of diol (FIGS. 12A-12C). Macromers with increased amount of FA in their backbone may have a greater degree of rigidity due to the increased presence of π bonds. Given this increased rigidity, the molecular chains can pack more densely as these chains have less degrees of freedom to rotate in space. Succinic acid, on the other hand, provides a single carbon-carbon bond which can freely rotate and prevent efficient packing and close alignment of chains. Therefore, less energy is required to break up interactions between chains and transition from a solid to liquid phase. In addition to packing efficiency, $T_m$ and $T_c$ also depend on molecular weight and the chain end concentration, factors that differed between groups (FIGS. 11B-11C). Over the range of temperatures tested (−70-120° C.), a glass transition temperature was not observed (FIG. 12A) among any of the groups.

Example 3: Formation of Crosslinked Networks

Figure 7:
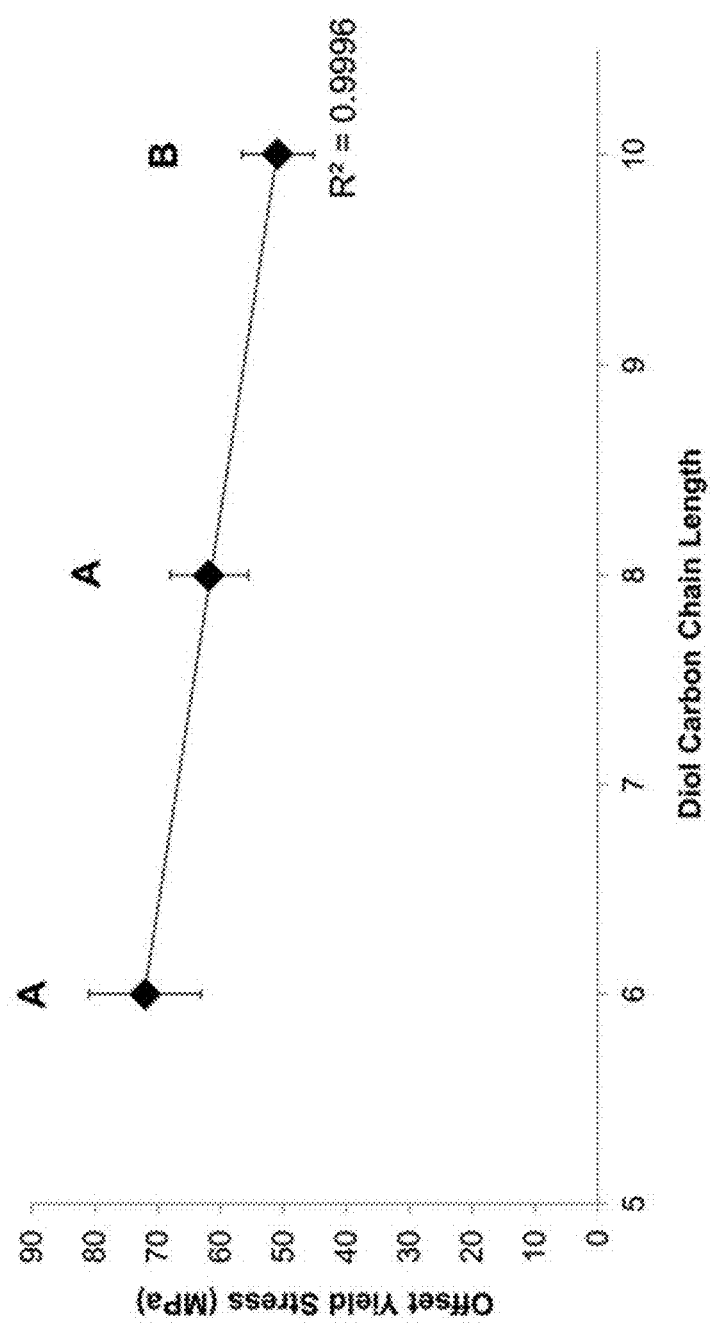
FIG. 7 is a graphical representation of compression data of networks consisting of unsaturated PDFs of differing diol chain lengths. Groups which do not share a letter are statistically significant ($p<0.05$). $R^2=0.9996$.

Scaffolds of crosslinked PDF networks (those used for FIG. 7) were fabricated by mixing the polymers with crosslinker (n-vinyl-2-pyrrolidinone, 1:1 mass ratio) and a bisacyl phosphine photoinitiator (Irgacure 819). The effects of different diols and availability of double bonds on the resulting Fourier Transform Infrared spectra, swelling ratios, and compressive properties of these networks were measured. For compressive testing, a mixture of PDF, crosslinker, and photoinitiator was poured into cylindrical molds (3 mm in diameter, 6 mm in height), exposed to blue light for 160 seconds to initiate crosslinking, and then compressed at a crosshead speed of 1 mm/min. FIG. 7 shows that as diol carbon chain length increases, the offset yield stress (MPa) decreases.

Disc constructs were fabricated to demonstrate the ability of the diol-based macromers to form crosslinked networks, using NVP as a crosslinker as has previously been explored in fumarate-based macromers. Purified polymer was dissolved NVP in a 1:1 wt/wt ratio. Photoinitiator (Irgacure 819) was added to the mixture (0.1 wt %). The mixture was then placed in polytetrafluoroethylene disc molds (6 mm in diameter, 1 mm in height) and exposed to blue light from an LED-based dental curing system (5 W Ogeee M115 LED curing light with emission range 420 to 480 nm, peak power 1500 mW/cm2) positioned 3.5 cm above the molds for 40 seconds to initiate crosslinking (n=5 discs per group in Table 3). These discs were then dried and stored under vacuum at room temperature.

Figure 13:
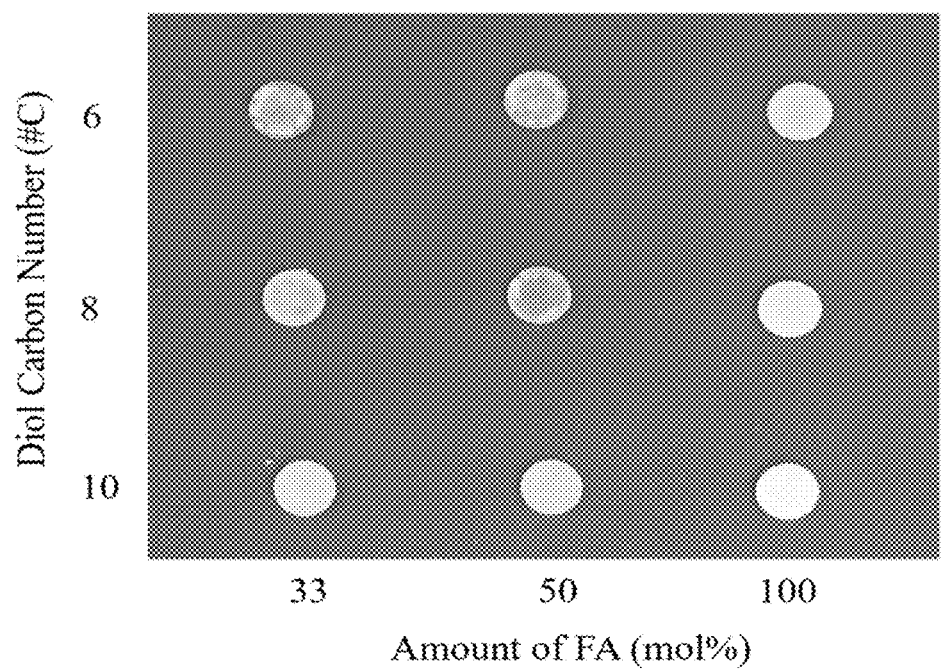
FIG. 13 depicts a gross image of disc constructs fabricated from photocrosslinked diol-based macromer networks taken before swelling experiments. Left-to-right: increasing amount of FA. Top-to-bottom: increasing diol carbon number.

Crosslinked networks of diol-based macromers were successfully formed by photocrosslinking. In gross appearance, discs ranged from an opaque white color to translucent, with increasing translucency with decreasing amount of FA and decreasing diol carbon number (FIG. 13). Gross handling properties ranged from a stiff, non-brittle material to an elastomeric material, with increasing elasticity with decreasing amount of FA. Both the relative translucency and elasticity upon handling of the material were observed to increase when discs were swollen. These crosslinked constructs were not soluble in water, acetone, dichloromethane, chloroform, or toluene (uncrosslinked polymers were slightly soluble in acetone and soluble in dichloromethane, chloroform, and toluene).

Swelling and Sol Fraction of Networks

The sol fraction, or soluble fraction, and swelling were measured and calculated per established methods in both an organic environment (toluene) and aqueous environment (PBS, pH=7.4). Toluene was chosen due to its ability to swell diol-based networks without disrupting their geometry or leading to degradation by hydrolysis. PBS was chosen due to its similar ionic composition to biological fluid. Discs (n=5 per group per solution) were individually incubated in an excess of solution (20 mL) under mild agitation. For toluene, discs were incubated at ambient temperature for 168 hours (1 week). For PBS, discs were incubated at 37° C. (physiologic temperature) for only 24 hours to minimize potential hydrolytic degradation. Discs were weighed before incubation (initial dry weight, $W_i$), immediately following incubation (swollen weight, $W_s$), and after being dried by vacuum at ambient temperature following incubation (final dry weight, $W_f$). Swelling (SW) and sol fraction (SF) were calculated as shown in Equations 2 and 3, respectively.

$$\text{Swelling} = SW = \frac{W_s - W_f}{W_f} \times 100\% \quad \text{(Eq. 2)}$$

$$\text{Sol Fraction} = SF = \frac{W_i - W_f}{W_i} \times 100\% \quad \text{(Eq. 3)}$$

Figure 14A:
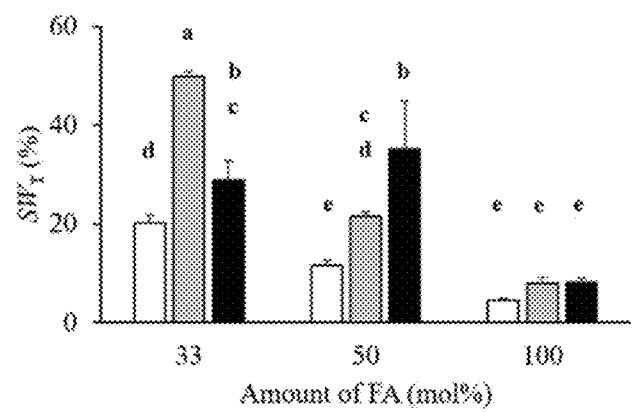
FIG. 14A shows the swelling of macromer networks in toluene. Error bars represent standard deviation. Those that do not share the same letter are significantly different (p<0.05).
Figure 14B:
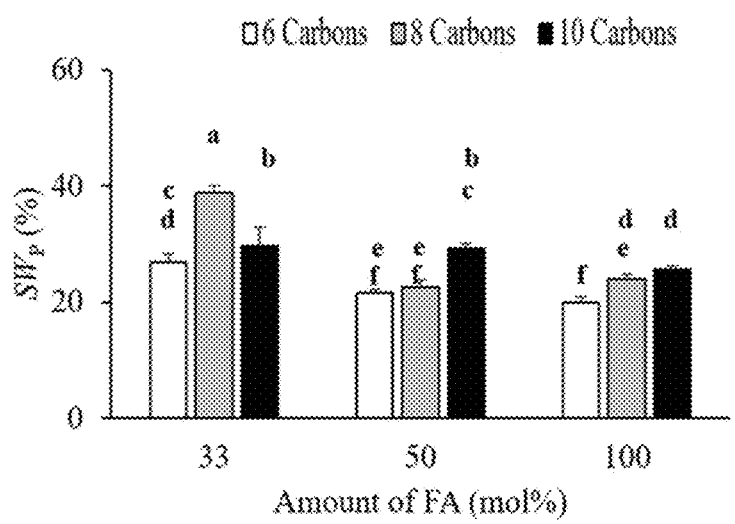
FIG. 14B shows the swelling of macromer networks in PBS. Error bars represent standard deviation. Those that do not share the same letter are significantly different (p<0.05).
Figure 14C:
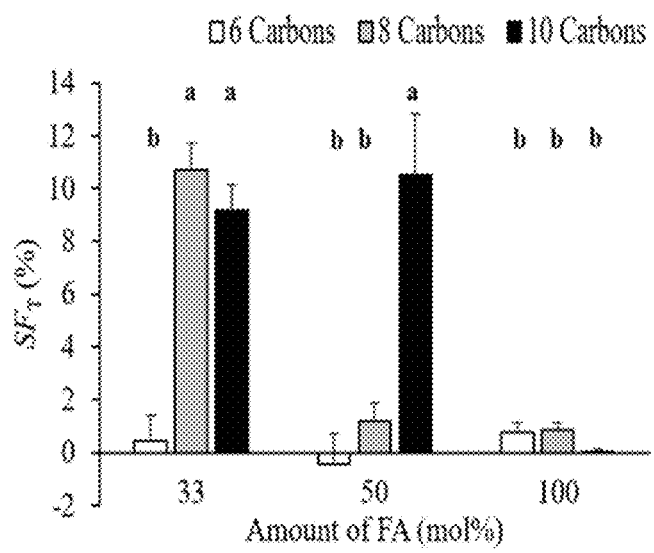
FIG. 14C shows the sol fraction of macromer networks in toluene. Error bars represent standard deviation. Those that do not share the same letter are significantly different (p<0.05).
Figure 14D:
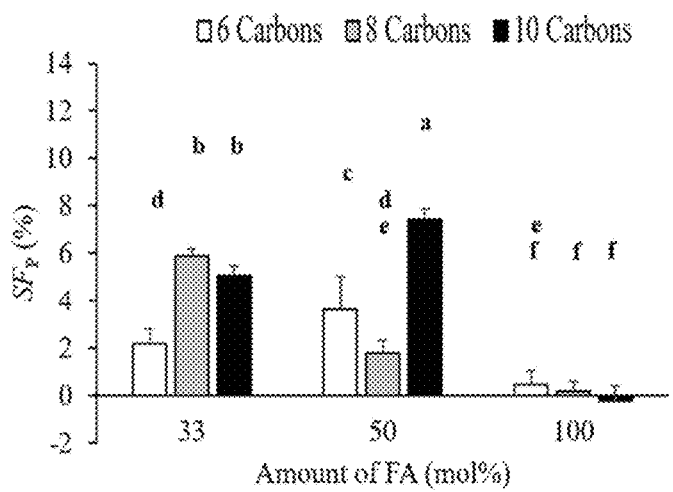
FIG. 14D shows the sol fraction of macromer networks in PBS. Error bars represent standard deviation. Those that do not share the same letter are significantly different (p<0.05).
Figure 15:
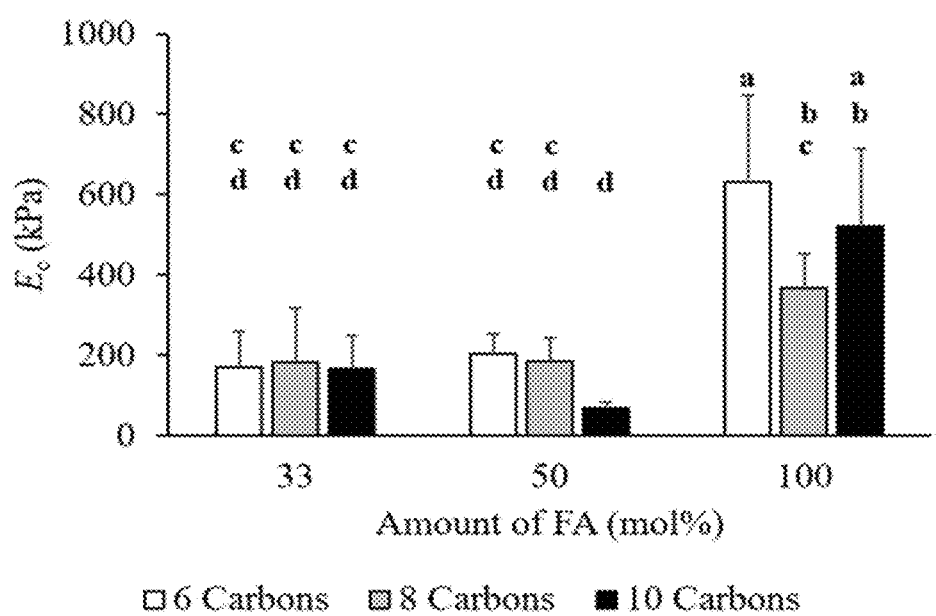
FIG. 15 shows the macromer network compressive modulus for different macromers. Error bars represent standard deviation. Those that do not share the same letter are significantly different (p<0.05).

The swelling and sol fraction for crosslinked networks prepared from the polymers are summarized in Table 4. Values are reported as mean±standard deviation. Within the same column, those that do not share the same letter are significantly different (p<0.05). Network swelling in an organic environment with no hydrolytic activity (toluene at ambient temperatures for 168 hours) ranged from 4.5±0.5 to 49.7±1.2% (P6F100 and P8F33, respectively) and generally increased with increasing diol carbon number and decreased with decreasing amount of FA (FIG. 14A). Network swelling under simulated physiologic conditions (PBS at 37° C. for 24 hours) ranged from 20.0±1.0 to 38.8±1.2% (P6F100 and P8F33, respectively) and increased with increasing diol carbon number and decreased with decreasing amount of FA (FIG. 14B). The sol fraction in toluene ranged from −0.5±1.2 to 10.7±1.0% (P6F50 and P8F33, respectively) and was significantly greater in P8F33, P10F50, and P10F33 compared to the other six groups (FIG. 14C). The sol fraction in PBS ranged from −0.2±0.6 to 5.9±0.3% (P10F100 and P8F33, respectively). Generally, decreased amount of FA resulted in increased sol fraction in PBS (FIG. 14D).

compressive modulus (FIG. 15). The measured moduli ranged from 69.7±14.2 to 633.4±214.1 kPa (P10F50 and P6F100, respectively). In general, groups with less than 100 mol % FA had decreased compressive modulus (FIG. 15). Per a statistical model built from the macromer network data, increasing diol carbon number had no effect on compressive modulus and increasing amount of FA significantly increased network compressive modulus (Table 6).

Networks constructed from macromers with 100 mol % FA had greater compressive moduli than networks with

TABLE 4

| Network Polymer | $SW_T$ (%) | $SW_P$ (%) | $SF_T$ | $SF_P$ | $E_c$ (kPa) |
|---|---|---|---|---|---|
| P6F33  | 20.2 ± 1.6$^d$  | 26.8 ± 1.5$^{c,d}$ | 0.4 ± 1.0$^b$  | 2.2 ± 0.6$^d$    | 171.9 ± 89.4$^{c,d}$ |
| P6F50  | 11.6 ± 1.0$^e$  | 21.5 ± 0.8$^{e,f}$ | −0.5 ± 1.2$^b$ | 3.7 ± 1.3$^c$    | 204.5 ± 49.8$^{c,d}$ |
| P6F100 | 4.5 ± 0.5$^e$   | 20.0 ± 1.0$^f$     | 0.8 ± 0.4$^b$  | 0.5 ± 0.6$^{e,f}$ | 633.4 ± 214.1$^a$ |
| P8F33  | 49.7 ± 1.2$^a$  | 38.8 ± 1.2$^a$     | 10.7 ± 1.0$^a$ | 5.9 ± 0.3$^b$    | 181.9 ± 136.7$^{c,d}$ |
| P8F50  | 21.6 ± 0.8$^{c,d}$ | 22.6 ± 1.2$^{e,f}$ | 1.2 ± 0.7$^b$  | 1.8 ± 0.6$^{d,e}$ | 185.4 ± 58.1$^{c,d}$ |
| P8F100 | 7.9 ± 1.3$^e$   | 24.1 ± 0.7$^{d,e}$ | 0.9 ± 0.3$^b$  | 0.2 ± 0.4$^f$    | 367.1 ± 85.5$^{b,c}$ |
| P10F33 | 28.9 ± 3.9$^{b,c}$ | 29.7 ± 3.1$^b$  | 9.2 ± 0.9$^a$  | 5.1 ± 0.4$^b$    | 167.2 ± 82.2$^{c,d}$ |
| P10F50 | 35.2 ± 9.6$^b$  | 29.3 ± 0.8$^{b,c}$ | 10.5 ± 2.3$^a$ | 7.4 ± 0.5$^a$    | 69.7 ± 14.2$^d$ |
| P10F100 | 8.1 ± 0.8$^e$  | 25.5 ± 0.6$^d$     | 0.0 ± 0.1$^b$  | −0.2 ± 0.6$^f$   | 521.3 ± 192.7$^{a,b}$ |

As a surrogate for crosslinking density, network swelling decreases with increased amount of crosslinking within a network. Greater amounts of succinic acid within the polymer backbone resulted in significantly greater network swelling in both toluene and PBS (Table 4 and FIGS. 14A-14B). As succinate cannot be used to form crosslinks between chains, networks with succinate substituting for fumarate have a lower potential crosslinking density. Greater diol carbon number (length) also resulted in greater swelling. With greater diol length, there is a larger distance between potential crosslinking sites in a chain; for example, in P6F100, there are 6 carbons between each fumarate group, while in P10F100, there are 10 carbons between each fumarate group. This increases the final network mesh size. Therefore, networks of P6F100 may have a greater crosslinking density as chains can pack more closely together due to proximity of fumarate groups. Sol fraction reflects the amount of macromer that is not crosslinked into a network and thus can freely diffuse out of the network once crosslinking is complete. In this study, decreased amount of FA (decreasing the amount of available unsaturated bonds) resulted in networks with greater sol fraction (FIGS. 14C-14D). Again, as succinate does not have unsaturated bonds available for free radical-initiated crosslinking, it follows that macromers with greater succinic acid have more chains that cannot become incorporated within a crosslinked network.

Compressive Modulus of Networks

The compressive modulus ($E_c$) was measured in a non-destructive assay using a thermomechanical analyzer (TA Instruments). Discs (n=5 per group) which had been swollen in PBS for 24 hours at 37° C. under mild agitation were subjected to a compressive force of 0.1 N/min over 0.01 N-0.25 N at 37° C. The rate of dimension change as a function of applied force was measured and the compressive modulus was calculated for each network based on the macromers in Table 3 using the software TA Advantage Control and Universal Analysis (TA Instruments).

Discs synthesized from diol-based photocrosslinked networks were swollen under simulated physiologic conditions (PBS, pH=7.4, at 37° C. under mild agitation) for 24 hours. Swollen discs were compressed at 37° C. to calculate incorporation of succinic acid. These results further suggest that the double bond density is greater in these polymers, allowing for more crosslinking and stronger network mechanical properties. Diol carbon number did not significantly affect compressive modulus in this model (see statistical analysis and Table 6). As diol carbon number has been suggested to correlate with the antimicrobial properties of diols, the decoupling of diol carbon number and compressive modulus may be advantageous for the development of macromer systems desired as inherently antimicrobial scaffolds, pharmaceutical compositions or drug delivery systems.

Statistical Analysis

All statistics in the foregoing examples were performed with the software JMP Pro 11 (SAS Institute, Cary, N.C.). All tests were conducted at the 5% significance level ($\alpha$=0.05). A one-way analysis of variance (ANOVA) test was performed (with posthoc analysis by Tukey's Honestly Significant Difference (HSD) test to compare $M_n$, $M_w$, PI, $RU_n$, $RU_w$, $T_m$, $T_c$, $T_g$, SW, SF, and $E_c$ between groups.

To better understand the relationship between monomer input parameters (diol carbon number and amount of FA in dicarboxylic acid feed) on final macromer and network physicochemical properties (outputs), a linear regression model was fit via standard least squares using all of the raw data (n=3 technical replicates from each of the nine syntheses in Table 3 for macromer properties, n=5 experimental replicates from networks fabricated from each of the nine syntheses in Table 3).

In the statistical model of the polymers (Table 5), both monomer input parameters (diol carbon number and amount of FA) significantly affected molecular weight and number of repeating units. Estimates are the predicted change in the property per each additional carbon in the diol or per each additional 1 mol % FA in the monomer feed. SEM=standard error of the mean. * denotes significant effect size of the input parameter (diol carbon number or amount of FA) on the final macromer property ($M_n$, $M_w$, etc) (p<0.05). Increasing diol carbon number increased macromer molecular weight and number of repeating units; increasing amount of FA decreased macromer molecular weight and number of repeating units. However, only amount of FA significantly affected (increased) the number of unsaturated bonds per macromer chain. There were no significant interactions between the two factors.

Table 6 summarizes the statistical model based on macromer network data. Estimates are the predicted change in the property per each additional carbon in the diol or per each additional 1 mol % FA in the monomer feed. SEM=standard error of the mean. * denotes significant effect size of the input parameter (diol number of carbons or amount of FA) on the final network property ($SW_T$, $SW_P$, etc) (p<0.05). The model suggests that increasing diol carbon number significantly increased swelling and sol fraction in both organic and aqueous solutions. Increasing amount of FA significantly decreased swelling and sol fraction in both solutions.

This model gave descriptive data (statistical significance of input parameters on final properties) but may also be of different ratios of dicarboxylic acids. These macromers were characterized to determine the effect of diol length and amount of unsaturated bonds on physicochemical properties. Macromers were then crosslinked to form three-dimensional networks. These networks were further characterized by measuring swelling and sol fraction in aqueous and organic solutions and compressive moduli under physiologic conditions. It was demonstrated that by controlling the two input parameters (diol carbon number and amount of FA) through the selection of different monomers, macromers with a range of physicochemical properties could be successfully synthesized. This range of properties extended to the subsequent three-dimensional networks built from these macromers. Given the ability to control polymer properties based on synthesis parameters, these diol-based aliphatic polyesters may serve as a flexible platform for tissue engineering and drug delivery strategies.

TABLE 5

| | Intercept | | | Diol Number of Carbons (#C) | | | Amount of FA (mol %) | | | Interactions | | |
|---|---|---|---|---|---|---|---|---|---|---|---|---|
| Property | Estimate | SEM | p | Estimate | SEM | p | Estimate | SEM | p | Estimate | SEM | p |
| $M_n$ (kDa) | 1.755 | 0.453 | <0.001* | 0.441 | 0.051 | <0.001* | −0.025 | 0.003 | <0.001* | −0.003 | 0.002 | 0.051 |
| $M_w$ (kDa) | 2.250 | 0.521 | <0.001* | 0.636 | 0.059 | <0.001* | −0.016 | 0.003 | <0.001* | −0.002 | 0.002 | 0.3862 |
| PI | 1.464 | 0.076 | <0.001* | −0.028 | 0.008 | 0.004* | 0.008 | <0.001 | <0.001* | <0.001 | <0.001 | 0.2983 |
| $RU_n$ | 13.656 | 1.868 | <0.001* | 0.950 | 0.210 | <0.001* | −0.100 | 0.012 | <0.001* | −0.009 | 0.007 | 0.229 |
| $RU_w$ | 20.362 | 2.167 | <0.001* | 1.156 | 0.244 | <0.001* | −0.064 | 0.014 | <0.001* | −0.003 | 0.009 | 0.699 |
| $B_n$ | 1.381 | 1.374 | 0.3253 | 0.293 | 0.155 | 0.071 | 0.076 | 0.009 | <0.001* | 0.007 | 0.005 | 0.189 |
| $B_w$ | −0.537 | 1.501 | 0.7240 | 0.343 | 0.169 | 0.054 | 0.230 | 0.010 | <0.001* | 0.016 | 0.006 | 0.011* |
| $T_m$ (° C.) | 51.755 | 2.610 | <0.001* | −0.442 | 0.294 | 0.146 | 0.411 | 0.017 | <0.001* | −0.051 | 0.010 | <0.001* |
| $T_c$ (° C.) | 37.526 | 2.938 | <0.001* | −0.683 | 0.331 | 0.051 | 0.389 | 0.019 | <0.001* | −0.065 | 0.012 | <0.001* |

TABLE 6

| | Intercept | | | Diol Number of Carbons (#C) | | | Amount of FA (mol %) | | | Interactions | | |
|---|---|---|---|---|---|---|---|---|---|---|---|---|
| Property | Estimate | SEM | p | Estimate | SEM | p | Estimate | SEM | p | Estimate | SEM | p |
| $SW_T$ (%) | 19.592 | 7.068 | 0.008* | 3.006 | 0.795 | <0.001* | −0.374 | 0.046 | <0.001* | −0.037 | 0.028 | 0.191 |
| $SW_P$ (%) | 21.902 | 3.457 | <0.001* | 1.369 | 0.389 | 0.001* | −0.105 | 0.022 | <0.001* | 0.005 | 0.014 | 0.724 |
| $SF_T$ (%) | −3.724 | 2.038 | 0.075 | 1.585 | 0.229 | <0.001* | −0.086 | 0.013 | <0.001* | −0.041 | 0.008 | <0.001* |
| $SF_P$ (%) | 3.101 | 1.225 | 0.015* | 0.495 | 0.138 | <0.001* | −0.068 | 0.008 | <0.001* | −0.015 | 0.005 | 0.003* |
| $E_c$ (kPa) | 113.053 | 112.885 | 0.323 | −20.976 | 12.706 | 0.106 | 5.456 | 0.730 | <0.001* | −0.284 | 0.447 | 0.5283 | value to the field based on its predictive power. The parameter estimates in Tables 5 and 6 are model coefficients. Essentially, the estimate for carbon number indicates the expected change in output per each additional carbon in the terminal diol, and the estimate for the amount of FA indicates the expected change in output per each additional 1 mol % FA in the total dicarboxylic acid monomer feed. For example, for macromer network swelling in toluene ($SW_T$), final macromer swelling is expected to increase 3.0% with each additional carbon in the terminal diol monomer and decrease 0.4% with each additional 1 mol % FA in the total dicarboxylic acid monomer feed. Currently, this model only applies to diol-based macromers with $C_6$-$C_{10}$ terminal diols and amount 33-100 mol % of FA.

As can be observed from the preceding examples, diol-based macromers were synthesized via a Fischer esterification of terminal diols and dicarboxylic acids. Nine variants were created by selecting diols of different lengths and Example 4: Testing of In Vitro Antifungal Activity

*A. fumigatus* Af293, *C. albicans* Y4215 and *Rhiozpus oryzae* R0969, all clinical isolates of pathogenic species, were used to determine the antifungal activity of three different terminal diols: 1,6-hexanediol; 1,8-octanediol; and 1,10-decanediol (all purchased from Sigma-Aldrich, St. Louis, Mo.). Briefly, minimum inhibitory concentration (MIC) was determined following the Clinical Laboratory & Standards Institute (CLSI) M38-A2 broth microdilution antifungal susceptibility testing method. Concentrations of diols from 1024 µg/mL to 0.0625 µg/mL were analyzed for fungal inhibition. The experiment was performed in triplicate for each species and each diol.

The MIC of three diols of different lengths (6, 8, and 10 carbons) were tested against three pathogenic fungal species (*A. fumigatus*, *C. albicans*, and *R. oryzae*) in triplicate (summarized in Table 7). In the table, R=resistant (no inhibition observed at 1,024 µg/mL or less). 1,6-hexanediol and 1,8-octanediol did not demonstrate activity against any species. 1,10-decanediol had MIC of 256 µg/mL against *A. fumigatus* and 1,024 µg/mL against *R. oryzae*.

TABLE 7

| Diol | C. albicans | A. fumigatus | R. oryzae |
|---|---|---|---|
| 1,6-Hexanediol | R | R | R |
| 1,8-Octanediol | R | R | R |
| 1,10-Decanediol | R | 256 µg/mL | 1,024 µg/mL |

Polymer Synthesis

Figure 16A:
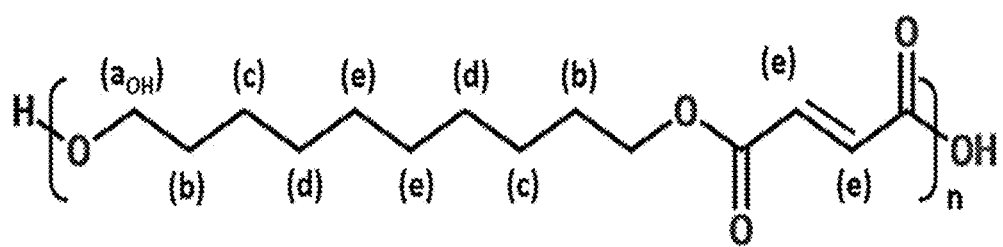
FIG. 16A depicts the structure of poly(decadediol-co-fumarate) of n units.
Figure 16B:
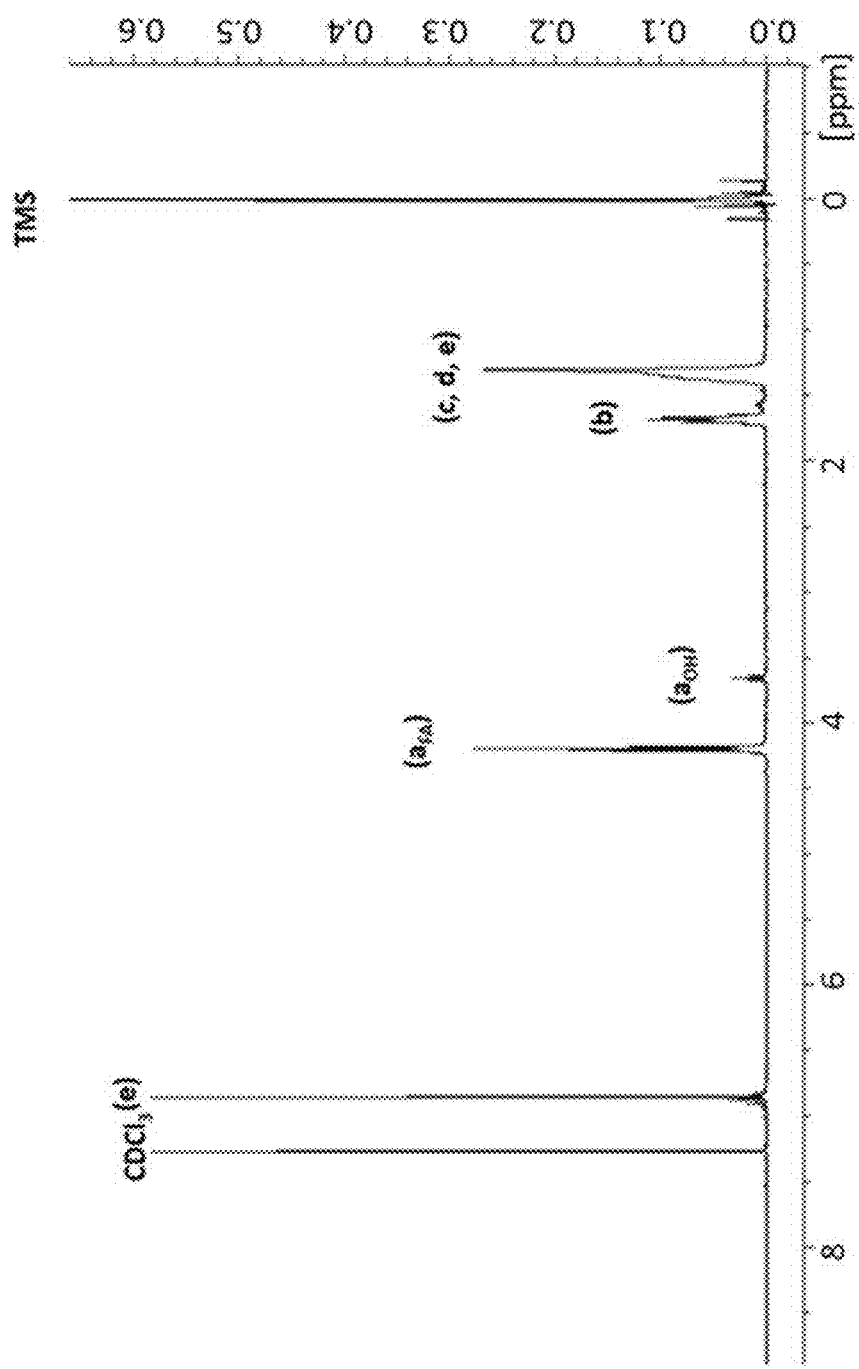
FIG. 16B shows the representative $^1$H-NMR spectroscopy of purified PDF corresponding to the structure shown in FIG. 16A. The peaks marked $a_{FA}$ and $a_{OH}$ represent protons on carbons adjacent to ester bonds and terminal alcohols, respectively.

Based on monomer antifungal activity (Table 107), 1,10-decanediol was selected for polymerization to synthesize poly(decanediol-co-fumarate) (PDF) (Macromer shown in FIG. 16A). Three separate syntheses were undertaken. PDF synthesis and purification was confirmed by proton spectroscopy (FIG. 16B) and resulted in a white powder. After purification, the final product yield was 46.04%±2.83%.

Briefly, equimolar concentrations of diol and fumaric acid with 1 mol % PTSA were stirred under nitrogen at 120° C. for 24 hours. The raw product of this synthesis was then purified by phase separation and ether precipitation. Raw polymer was dissolved in an excess of dichloromethane (1:20 w/v) to produce an organic phase. This organic phase was placed in a separation funnel, mixed with an excess of Millipore water (1:2 v/v), and vigorously shaken to remove unreacted fumaric acid (as well as low molecular weight chain polymer). The organic phase was isolated and then reduced by rotary evaporation to recover the remaining polymer and unreacted organic-soluble diols. This powder was re-dissolved in dichloromethane (DCM) (1:5 w/v) and added dropwise to an excess of chilled ethyl ether (1:200 v/v). The purified polymer precipitated out of the ether and was recovered by filtration with a Grade 50 Whatman® filter. The purified polymer was vacuum dried and stored at ambient temperature while shielded from light. 10 mg of purified polymer was dissolved in deuterated chloroform (Sigma-Aldrich) and subjected to $^1$H-NMR spectroscopy using a 400 MHz spectrometer (Bruker, Billerica, Mass.) and analyzed with TOPSPIN 3.0 software (Bruker).

Microparticle Fabrication

Diol-based polymer microparticles were prepared by the oil/water (O/W) method. Briefly, 10 mg of voriconazole (VRC) (Sigma-Aldrich, St. Louis, Mo.) was added to 100 mg of purified polymer. One lot of polymer was randomly chosen from a total of three syntheses. For unloaded ("blank") microparticle groups, no VRC was added. The powders were then dissolved at room temperature under mild agitation in 0.4 mL DCM (Sigma-Aldrich, St. Louis, Mo.), resulting in a clear solution (oil phase). 0.8 mL of chilled 1 wt % poly(vinyl alcohol) (PVA) (Sigma-Aldrich, ST. Louis, Mo.) was added. The mixture was vortexed for 15 sec at room temperature, resulting in an opaque white suspension. This suspension was then poured into 25 mL of chilled 1 wt % PVA (water phase) stirring at 400 RPM. After pouring in the 1.2 mL of PDF/VRC/DCM/PVA, stirring rate was reduced to 200 RPM. The suspension was stirred for 3 hours to allow evaporation of DCM.

After 3 hours, microparticles were collected by centrifugation (3500 RPM for 3 minutes) and washed and centrifuged 3 times in 35 mL of chilled distilled water (for removal of excess PVA). The microparticles were then flash frozen using liquid nitrogen and lyophilized overnight. Three separate lots of loaded and unloaded microparticles were fabricated to demonstrate reproducibility. Microparticle diameter was characterized by analysis of bright field microscopy images using ImageJ (National Institutes of Health, Washington, D.C.).

Figure 17:
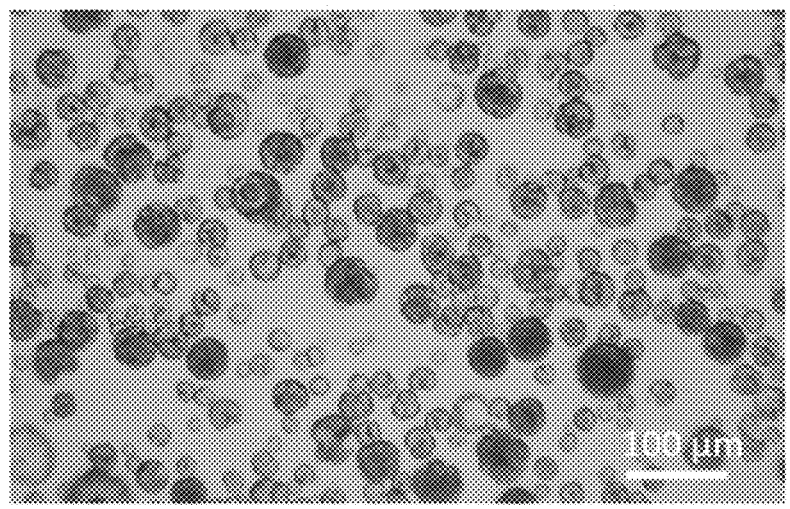
FIG. 17 shows a bright field microscopy image of VRC-loaded PDF microparticles. Scale bar=100 μm.

Fabrication resulted in about 70-90 mg microparticles per lot. Upon inspection under bright field microscopy (FIG. 17), microparticles had a spherical form with average size of 26.6±9.4 µm in diameter and ranged in size from 11.1 to 45.2 µm in diameter.

In Vitro Drug Release

After drying, 20 mg of microparticles (n=3 per loaded and unloaded group, each from a distinct fabrication lot) were placed in 5 mL Eppendorf tubes (VWR, Radnor, Pa.). The microparticles were placed in 2 mL PBS at pH=7.4 at 37° C. under mild agitation. At 6 hours, 12 hours, 24 hours, and every 24 hours thereafter, supernatant was collected and replaced with fresh PBS. The collected supernatant was filtered under sterile conditions and frozen until analysis by high performance liquid chromatography (HPLC).

Briefly, HPLC was performed using a 2695 separation module (Waters, Milford, Mass.), 2996 photodiode array detector (Waters), and a 250 mm×4.6 mm XTerra RP 18 column (Waters). Recovered supernatant was eluted through the column at a flow rate of 1 mL/min in an isocratic mobile phase (60% acetonitrile/40% 0.1% v/v trifluoroacetic acid) over 5 minutes per sample. Absorbance was measured at λ=254. A standard curve with VRC concentrations ranging from 0.1-200 µg/mL was prepared by dissolving 2 mg of VRC in 10 mL of PBS and performing serial dilutions. Data was analyzed with the software Empower (Waters, Milford, Mass.) and the cumulative release (sum of amount of VRC eluted up to each time point) as well as cumulative release per mg microparticle was calculated for each group at each time point.

Figure 18A:
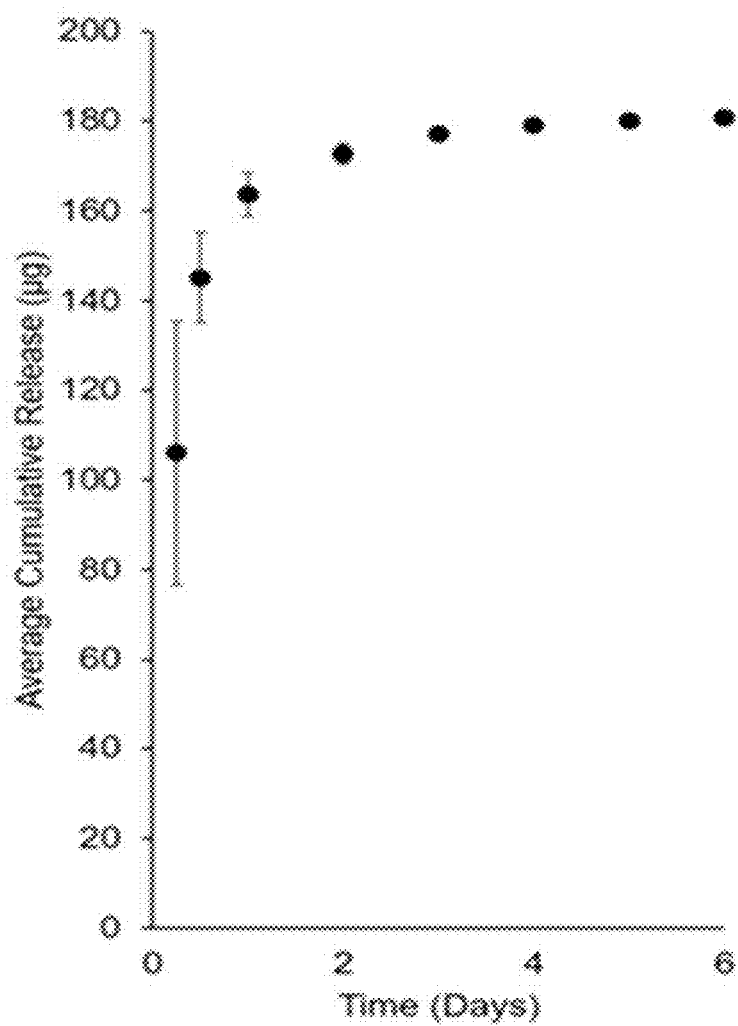
FIG. 18A depicts the release kinetics of VRC from 20 mg of diol-based microparticles loaded at 10 wt % VRC (n=3) as average cumulative release.
Figure 18B:
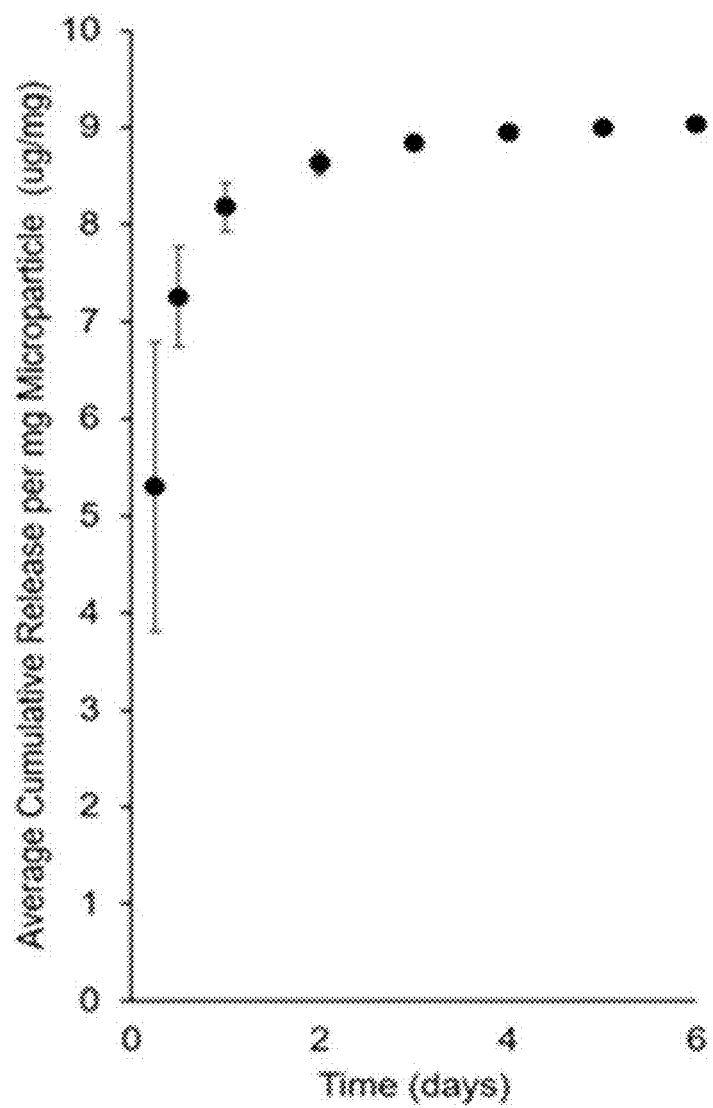
FIG. 18B depicts the release kinetics of VRC from 20 mg of diol-based microparticles loaded at 10 wt % VRC (n=3) as average cumulative release per mg microparticle.

Supernatant was collected and assayed over 6 days of incubation (the duration of treatment for subsequent murine studies) under physiologic conditions (PBS, pH=7.4, 37° C.). No VRC was detectable in blank microparticle groups. In VRC-loaded microparticles, a cumulative average of 180.78 µg was released over the 6 days (FIG. 18A). Cumulative average release per mg microparticle was 9.04 µg (FIG. 18B).

Example 5: Testing of In Vivo Antifungal Activity

All animal use was approved by the Animal Welfare Committee of the University of Texas MD Anderson Cancer Center. BALB/c mice of 18-22 g were subjected to a cyclophosphamide/cortisone acetate immunosuppression/neutropenia protocol as previously reported. Briefly, mice were given 200 µl interperitoneal injections of cyclosphosphamide (100 mg/kg) on Days −4, −1, +2, and +6, and a single subcutaneous dose of 100 µl cortisone acetate (250 mg/kg) on Day −1. Throughout immune suppression, mice were prophylactically provided with sucrose water with doxycycline to prevent potential bacterial superinfection. Five mice were kept per cage and individually tracked by marked tails. Cages were divided randomly into 4 groups (n=5 mice per group, performed in duplicate on different days, for total n=10 per group) based on fungal inoculation and treatment strategy. Table 11 summarizes the animal groups to evaluate the efficacy of diol-based polymer microparticle delivery for treatment of infected fungal defects (n=10). VRC=voriconazole and MP=microparticles.

TABLE 11

| Group | Group # | Description | Inoculum | Treatment |
|---|---|---|---|---|
| NO INF, NO TX | 1 | Positive Control | Saline | None |
| INF, NO TX | 2 | Negative Control | $1.75 \times 10^6$ conidia | None |
| INF, BLANK MP | 3 | Material Control | $1.75 \times 10^6$ conidia | Blank MPs |
| INF, VRC MP | 4 | Experimental Group | $1.75 \times 10^6$ conidia | VRC-loaded MPs |

On Day 0, the mice were shaven, prepped, and given 100 μl subcutaneous injections of saline or $1.75 \times 10^7$ conidia/mL of A. fumigatus Af293 (for a total of $1.75 \times 10^6$ conidia) over the right dorsal flank. A marker was used to denote the site of inoculation. On Day +3, a 5 mm biopsy punch was used to create a cutaneous defect over the site of inoculation. Mice were prophylactically given subcutaneous injections of 100 μl meloxicam (0.3 mg/kg) and 50 μl 0.25% bupivacaine. Cutaneous biopsy was performed with mice anesthetized via isoflurane. The wound was covered with a sterile strip of transparent surgical wound dressing (Tegaderm™, St. Paul, Minn.). The wound was then re-inoculated by injection under the wound dressing with 100 μl of $1.75 \times 10^7$ conidia/mL. For mice receiving blank or VRC-loaded microparticles, 5 mg of microparticles (sterilized by exposure to ethylene oxide gas) were added to the 100 μl of inoculum immediately preceding injection. Randomly selected specimens of harvested skin removed skin were placed dermis-side down on yeast extract agar glucose (YAG) plates for culture at 37° C. to determine tissue infection at Day +3 (5 specimens from Group 1, 10 specimens from mice from inoculated Groups 2-4). Mice were given 100 μl meloxicam (0.3 mg/kg) every 12 hours for three days following surgery. Mice were weighed daily starting on Day 0.

Twelve hours following surgery, photographs of the wound bed were taken of each mouse (Day +3). These photographs were repeated immediately preceding euthanasia (Day +9). Wound surface area was traced and measured with ImageJ. Mice were euthanized on Day +9 by $CO_2$ asphyxiation. A 10 mm×10 mm section of tissue around the wound bed was harvested by dissection under sterile conditions. Wounds were placed in 1.5 mL of sterile saline and homogenized under sterile conditions. 200 μl of a 1:100 dilution of homogenized wound beds was spread on YAG plates and incubated at 37° C. for 48 hours for CFU counting and analysis. Similarly, murine kidneys were harvested, stored in 1.5 mL saline, and homogenized. 200 μl (with no dilution) of homogenized kidney was spread on YAG plates and incubated at 37° C. for 48 hours for CFU counting and analysis to assay for potential hematogenous dissemination.

Figure 19:
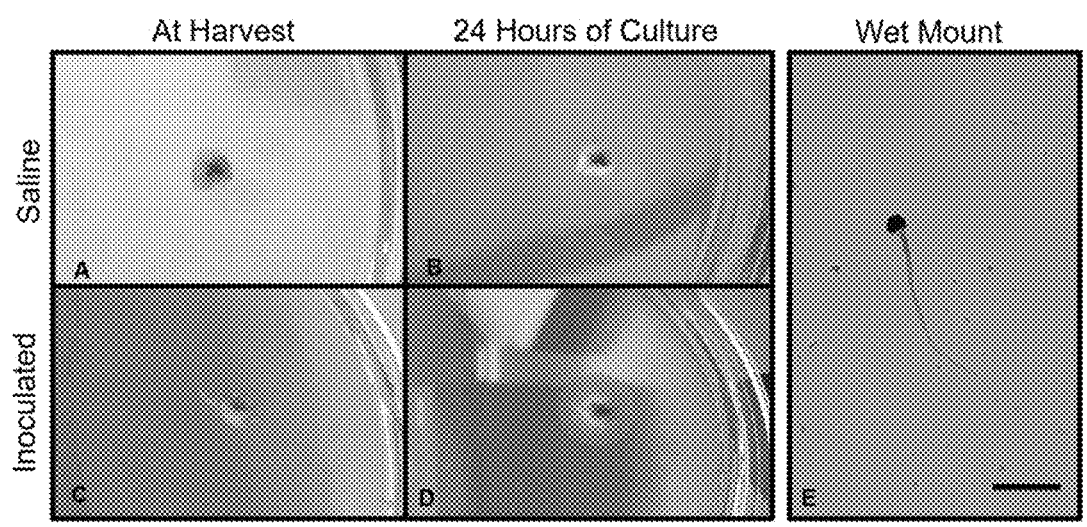
FIG. 19 shows mouse skin biopsies harvested during defect creation on Day +3. Representative tissue from non-inoculated (Saline) animals and inoculated animals, with a black mark created on Day 0 to mark the point of inoculation. Biopsies were placed on sterile agar dishes and incubated for 24 hours at 37° C. All saline groups demonstrated no growth. All inoculated groups demonstrated growth. On wet mount of culture from inoculated groups, conidia and conidiophores were observed. Scale bar=100 μm.

One day after subcutaneous inoculation (Day +1), there were no visible signs of infection. However, by Day +2, mice in conidia-containing groups demonstrated visible swelling at the site of injection. This area of gross inflammation persisted at Day +3 at the time of defect creation. In some mice in Groups 2-4, purulent discharge was observed in the wound. All plated skin biopsies taken at Day +3 from inoculated groups demonstrated A. fumigatus growth on culture (no growth from Group 1 skin biopsies) (FIG. 19).

During the course of the study, three mice died while under anesthesia (one each from Groups 1, 2, and 4) and one mouse had to be euthanized due to an injury sustained during a routine injection on Day +4 (Group 4). All other mice (N=36) survived until euthanasia at the terminal time point (Day +9). Mice tolerated the infected cutaneous lesion with no lameness or signs of systemic illness (reduced motor activity, lethargy, shivering, and piloerection). There were no significant differences in weight between groups at Day +9 (average weight=17.98±1.56 g). In addition, no fungi were detectable by culture of harvested homogenized kidneys for animals in any group.

Weight, wound surface area, and CFU counts of murine groups were compared by a one-way ANOVA with posthoc analysis via Tukey's Honestly Significant Difference test ($\alpha=0.05$) using JMP® Pro 11.0.0 (SAS Institute Inc., Cary, N.C.).

Figure 20A:
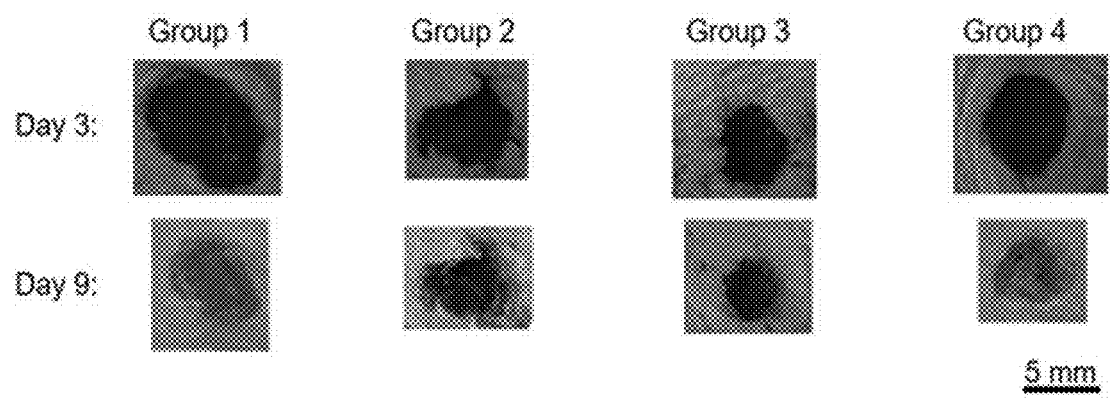
FIG. 20A shows gross photographs of murine cutaneous wounds 12 hours after surgery (Day +3) and immediately preceding euthanasia (Day +9). Scale bar=5 mm.
Figure 20B:
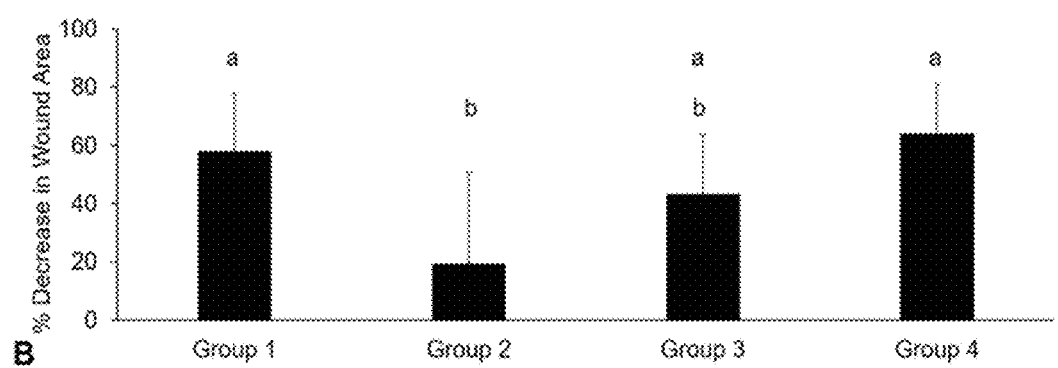
FIG. 20B depicts the average percentage decrease in wound surface area (n=9, 9, 10, and 8 for Groups 1, 2, 3, and 4, respectively). Error bars represent standard deviation. Those that do not share the same letter are statistically significantly different (p<0.05).

Photographs of the wounds were taken 12 hours after surgery (Day +3) and immediately before euthanasia (Day +9) (FIG. 20A). Average wound size decreased by 58.12, 19.40, 43.23, and 64.17% for Groups 1, 2, 3, and 4, respectively (FIG. 20B). While all groups demonstrated reduction in wound surface area on average, 2/9 mice in Group 2 had an increase in wound surface area (+18.31% and +21.22%). All other mice demonstrated reduction in wound size. Mice treated with VRC-loaded microparticles (Group 4) and non-infected mice (Group 1) both had significantly greater reduction in wound size compared to infected, non-treated animals (Group 2). Animals treated with blank microparticles (Group 3) demonstrated greater wound healing than Group 2 and less healing than mice in Groups 1 and 4; however, these trends with respect to Group 3 were not statistically significant.

Figure 21A:
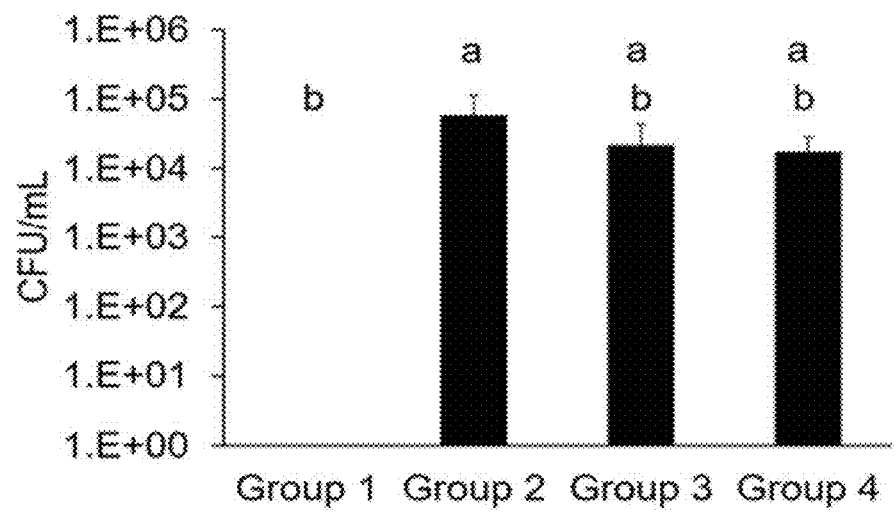
FIG. 21A depicts the CFU count normalized by volume (tissue harvested and homogenized in 1.5 mL sterile saline) shown on logarithmic scale (n=6, 6, 7, and 5 for Groups 1, 2, 3, and 4, respectively). Error bars represent standard deviation. Those that do not share the same letter are statistically significantly different (p<0.05).
Figure 21B:
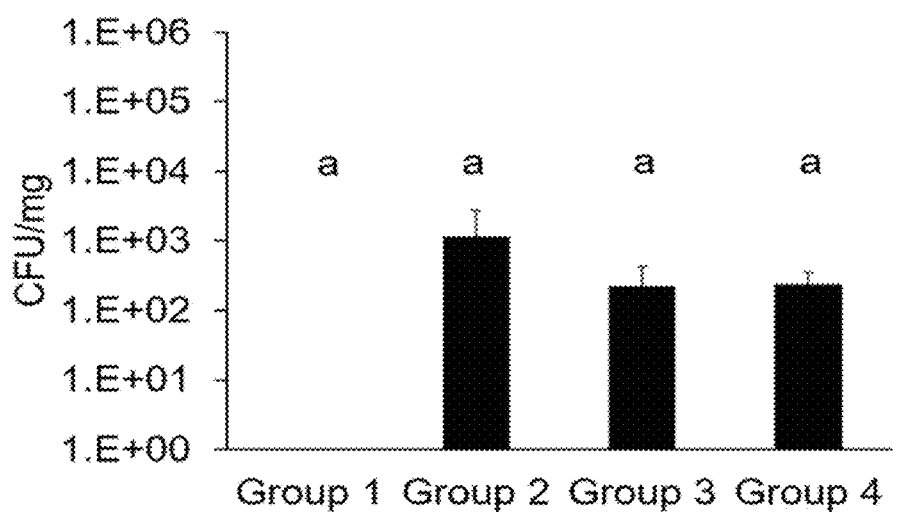
FIG. 21B depicts the CFU count normalized by tissue weight shown on logarithmic scale (n=6, 6, 7, and 5 for Groups 1, 2, 3, and 4, respectively). Error bars represent standard deviation. Those that do not share the same letter are statistically significantly different (p<0.05).

A 10 mm×10 mm section of tissue surrounding the cutaneous defect was harvested upon euthanasia and homogenized for CFU counting. In FIGS. 21A and 21B, CFU counts are presented as CFU/mL (with tissue specimens homogenized in 1.5 mL of sterile saline) or CFU/mg harvested tissue. Non-infected animals (Group 1) grew no colonies. Normalized by volume, Group 2 (non-treated) had significantly greater fungal burden than Group 1, with no significant differences between Groups 3 and 4 and the others. Normalized by tissue weight, there are no statistically significant differences between any groups. However, the trend of Group 2 having greater fungal burden than Groups 3 and 4 and no detectable fungi in Group 1 held true in all instances.

Although the foregoing invention has been described in some detail by way of illustration and example for purposes of clarity of understanding, one of skill in the art will appreciate that certain changes and modifications may be practiced within the scope of the appended claims. While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

What is claimed is:

1. A composition comprising a polymer comprising condensed units of an aliphatic terminal diol and an unsaturated dicarboxylic acid; wherein the terminal diol comprises from 6 to 10 methylene groups and the dicarboxylic acid comprises fumaric acid, and wherein the polymer further comprises condensed units of succinic acid.

2. The composition of claim 1 wherein the polymer is crosslinked.

3. The composition of claim 1 wherein the ratio of fumaric acid units to succinic acid units is from about 1:0.8 to about 1:4.

4. The composition of claim 1 wherein the polymer consists essentially of condensed units of the aliphatic terminal diol, fumaric acid and the condensed units of succinic acid.

5. The composition of claim 1 wherein the aliphatic terminal diol is selected from the group consisting of 1,6-hexanediol, 1,8-octanediol, or 1,10-decanediol.

6. The composition of claim 1 wherein the polymer is selected from the group consisting of poly(hexanediol fumarate-co-succinate), poly(octanediol fumarate-co-succinate), and poly(decanediol fumarate-co-succinate).

7. A composition comprising a polymer comprising condensed units of an aliphatic terminal diol and an unsaturated dicarboxylic acid; wherein the terminal diol comprises from 6 to 10 methylene groups and the dicarboxylic acid comprises fumaric acid, and wherein the composition further comprises a therapeutic agent as an active ingredient; and optionally, a pharmaceutically acceptable carrier and/or excipient or diluent.

8. The composition of claim 7 further comprising a pharmaceutical surfactant.

9. The composition of claim 7 further comprising a cryoprotectants.

10. The composition of claim 7 further comprising a pharmaceutically acceptable excipient.

11. The composition of claim 7 comprising a microparticle comprising the polymer.

12. The composition of claim 11 wherein the microparticle comprises the polymer and the therapeutic agent.

13. The composition of claim 7 wherein the therapeutic agent comprises a triazole antifungal agent.

14. A method for treatment of a subject suffering a fungal infection comprising applying a composition comprising a polymer and a therapeutic agent to the site of the fungal infection, wherein the polymer comprises condensed units of an aliphatic terminal diol and an unsaturated dicarboxylic acid; wherein the terminal diol comprises from 6 to 10 methylene groups and the dicarboxylic acid comprises fumaric acid, and wherein the therapeutic agent comprises a triazole antifungal agent.

15. The method of claim 14 wherein the fungal infection comprises aspergillosis, candidemia, candidiasis, mucormycosis, fusarium infection, or seedosporium infection.

16. The composition of claim 8, wherein the pharmaceutical surfactant is selected from the group consisting of a cationic surfactant, an anionic surfactant, a non-ionic surfactant, and combinations thereof.

17. The composition of claim 13, wherein the triazole antifungal agent is voriconazole.

18. The method of claim 14, wherein the polymer further comprises condensed units of succinic acid.

19. The method of claim 14, wherein the composition comprises a microparticle comprising the polymer and the therapeutic agent.

20. The method of claim 14, wherein the step of applying the composition is performed by application of a drug delivery device comprising the composition to the site of the fungal infection.

* * * * *